(12) United States Patent
Fairhurst et al.

(10) Patent No.: US 8,318,935 B2
(45) Date of Patent: Nov. 27, 2012

(54) ORGANIC COMPOUNDS 75074

(75) Inventors: Robin Alec Fairhurst, Horsham (GB); Rebecca Butler, Horsham (GB); Paul Oakley, Horsham (GB); Stephen Paul Collingwood, Horsham (GB); Nichola Smith, Horsham (GB); Emily Stanley, Horsham (GB); Maria Ines Rodriguez Perez, Biel-Benken (CH)

(73) Assignee: Novartis AG, Basel (CH)

( * ) Notice: Subject to any disclaimer, the term of this patent is extended or adjusted under 35 U.S.C. 154(b) by 276 days.

(21) Appl. No.: 12/451,152

(22) PCT Filed: May 5, 2008

(86) PCT No.: PCT/EP2008/055497
§ 371 (c)(1),
(2), (4) Date: Oct. 27, 2009

(87) PCT Pub. No.: WO2008/135557
PCT Pub. Date: Nov. 13, 2008

(65) Prior Publication Data
US 2010/0105660 A1    Apr. 29, 2010

(30) Foreign Application Priority Data
May 7, 2007    (EP) .................................... 07107654

(51) Int. Cl.
*C07D 401/14*    (2006.01)
*A61K 31/497*    (2006.01)
*A61P 11/06*    (2006.01)

(52) U.S. Cl. .................................. 544/357; 514/252.11
(58) Field of Classification Search .................. 544/357; 514/252.11
See application file for complete search history.

(56) References Cited

FOREIGN PATENT DOCUMENTS

| WO | WO 01/05773 | 1/2001 |
|---|---|---|
| WO | WO 2005/016879 | 2/2005 |
| WO | WO 2005/025496 | 3/2005 |

OTHER PUBLICATIONS

Krafte et al., Current Opinion in Pharmacology 2008, 8:50-56.*
Rush et al., Molecular Interventions 2007, vol. 4, issue 7, 192-195.*
Dermer et al., Bio/Technology, 1994, 12:320.*
Freshney et al.,Culture of Animal Cells, A Manual of Basic Technique, Alan R. Liss, Inc., 1983, New York, p. 4.*
Clare et al, Drug Discovery Today 2000, vol. 5, No. 11,506-520.*

* cited by examiner

*Primary Examiner* — Venkataraman Balasubramanian
(74) *Attorney, Agent, or Firm* — Mark W. Milstead

(57) ABSTRACT

A compound of formula (I), or tautomers, or stereoisomers, or solvates, or pharmaceutically acceptable salts thereof, wherein $M_1$, $M_2$, $L_1$, $L_2$, $W_1$, $W_2$, $X_1$, $X_2$, $Y_1$, $Y_2$, A, $R^5$ and $R^{5a}$ are as defined herein for the for treatment of conditions treatable by the blockade of an epithelial sodium channel, particularly conditions benefiting from mucosal hydration.

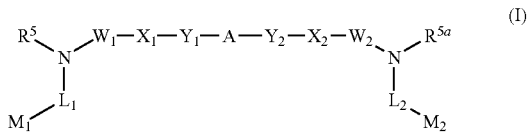

(I)

19 Claims, No Drawings

ORGANIC COMPOUNDS 75074

This is a 35 U.S.C. 371 National Stage application based on International Patent Application No. PCT/EP08/055497, filed 5 May 2008, this application further claims benefit under 35 U.S.C. §119(a)-(d) or (f) or 365(b) of European Patent Application No. 07107654.1, filed May 7, 2007, the contents of which are incorporated herein by reference in their entirety.

This invention relates to organic compounds, their preparation and use as pharmaceuticals.

In one aspect, the present invention provides compounds of formula (I):

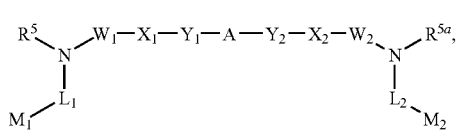

or tautomers, or stereoisomers, or solvates, or pharmaceutically acceptable salts thereof, wherein $M_1$ and $M_2$ are independently

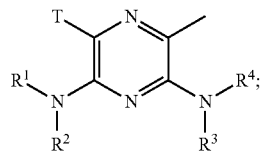

$R^1$, $R^2$, $R^3$, and $R^4$ are independently selected from H, $C_1$-$C_8$-alkyl, $C_1$-$C_8$-alkyl-carboxy, $C_1$-$C_8$-haloalkyl, $C_3$-$C_{15}$-carbocyclic group, $C_1$-$C_8$-alkylcarbonyl, $C_1$-$C_8$-alkoxycarbonyl, a $C_6$-$C_{15}$-membered aromatic carbocyclic group, a 4- to 14-membered heterocyclic group, a $C_1$-$C_8$-alkyl substituted by a 4- to 14-membered heterocyclic group, and a $C_1$-$C_8$-alkyl substituted by a $C_6$-$C_{15}$-membered aromatic carbocyclic group, or $R^1$ and $R^2$ with the nitrogen atom to which they are attached form a $C_3$-$C_{14}$-membered heterocyclic group optionally substituted by $R^{14}$, or $R^3$ and $R^4$ with the nitrogen atom to which they are attached form a $C_3$-$C_{14}$-membered heterocyclic group optionally substituted by $R^{14}$;

$L_1$ and $L_2$ are independently selected from:

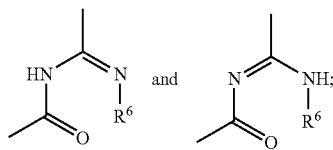

$R^6$, $R^5$ and $R^{5a}$ are independently selected from H, $C_1$-$C_8$-alkyl, $C_1$-$C_8$-alkyl-carboxy, $C_1$-$C_8$-alkyl-alkoxy, $C_1$-$C_8$-haloalkyl, $C_3$-$C_{15}$-carbocyclic group, $C_1$-$C_8$-alkylcarbonyl, $C_1$-$C_8$-alkoxycarbonyl, nitro, cyano, a $C_6$-$C_{15}$-membered aromatic carbocyclic group, a 4- to 14-membered heterocyclic group, a $C_1$-$C_8$-alkyl substituted by a 4- to 14-membered heterocyclic group, and a $C_1$-$C_8$-alkyl substituted by a $C_6$-$C_{15}$-membered aromatic carbocyclic group;

$W_1$ and $W_2$ are independently selected from $C_0$-$C_8$-alkylene;

$X_1$ and $X_2$ are independently selected from a 4- to 14-membered heterocyclic group;

$Y_1$ and $Y_2$ are independently —$C_0$-$C_8$-alkylene-; or $C_1$-$C_8$-alkylamino;

A is selected from a $C_6$-$C_{15}$-membered aromatic carbocyclic group, —CONR$^{11a}$—($C_1$-$C_8$-alkylene)-NR$^{11a}$CO—, —CO—($C_1$-$C_8$-alkylene)-CO—, —CO—($C_1$-$C_8$-alkenylene)-CO—, —(C═O), —CO—($C_0$-$C_8$-alkylene)-Z—($C_0$-$C_8$-alkylene)-CO—, —CONR$^{11a}$—($C_0$-$C_8$-alkylene)-Z—($C_0$-$C_8$-alkylene)-NR$^{11a}$CO—, $C_3$-$C_{15}$-carbocyclic group and a 4- to 14-membered heterocyclic group;

Z is selected from $C_6$-$C_{15}$-membered aromatic carbocyclic group, $C_3$-$C_{15}$-carbocyclic group and a 4- to 14-membered heterocyclic group;

T is selected from H, halogen, $C_1$-$C_8$-alkyl, $C_1$-$C_8$-haloalkyl, $C_1$-$C_8$-haloalkoxy, $C_3$-$C_{15}$-carbocyclic group, nitro, cyano, a $C_6$-$C_{15}$-membered aromatic carbocyclic group, a and a $C_1$-$C_8$-alkyl substituted by a $C_6$-$C_{15}$-membered aromatic carbocyclic group;

wherein each $C_6$-$C_{15}$-membered aromatic carbocyclic group and each 4- to 14-membered heterocyclic group or 5- to 14-membered heterocyclic group, unless otherwise specified is independently optionally substituted by one or more groups selected from OH, $C_1$-$C_8$-alkoxy, $C_1$-$C_8$-alkyl, halogen, SO$_2$NR$^{11}$R$^{12}$, hydroxy$C_1$-$C_8$-alkoxy optionally substituted by hydroxyl, ($C_0$-$C_4$-alkylene)CONR$^{11}$R$^{12}$, ($C_0$-$C_4$-alkylene)-N═C(NR$^{11}$R$^{12}$)$_2$), —O—($C_1$-$C_4$-alkylene)-N═C(NR$^{11}$R$^{12}$)$_2$, —O—($C_1$-$C_4$-alkylene)-CONR$^{11}$R$^{12}$, $C_7$-$C_{10}$-aralkoxy, $C_7$-$C_{10}$-aralkyl, SH, S($C_1$-$C_8$-alkylene), SO$_2$($C_1$-$C_8$-alkylene), SO($C_1$-$C_8$-alkylene), NR$^{11}$R$^{12}$, NR$^{11}$($C_{3-12}$-carbocyclic group) where the carbocyclic group is optionally substituted by halogen or $C_1$-$C_8$-alkyl, R$^{15}$, a $C_1$-$C_8$-alkyl substituted by R$^{15}$, R$^{16}$, a $C_1$-$C_8$-alkyl substituted by R$^{16}$, O($C_1$-$C_8$-alkylene)-NR$^{11}$—(C═O) O—($C_0$-$C_4$-alkylene)-R$^{15}$, cyano, oxo, carboxy, nitro, $C_1$-$C_8$-alkylcarbonyl, hydroxy-$C_1$-$C_8$-alkyl, $C_1$-$C_8$-haloalkyl, amino-$C_1$-$C_8$-alkyl, amino(hydroxy)$C_1$-$C_8$-alkyl and $C_1$-$C_8$-alkoxy optionally substituted by aminocarbonyl, where R$^{15}$ is a $C_6$-$C_{15}$-membered aromatic carbocyclic group, optionally substituted by OH, $C_1$-$C_8$-alkoxy, $C_1$-$C_8$-alkyl, halogen and $C_1$-$C_8$-haloalkyl, R$^{16}$ is a 4- to 14-membered heterocyclic group, optionally substituted by OH, $C_1$-$C_8$-alkoxy, $C_6$-$C_{15}$-membered aromatic carbocyclic group, CO$_2$H, (C═O)-3 to 14-membered heterocyclic group, halogen and $C_1$-$C_8$-haloalkyl, and wherein each alkylene group, unless otherwise specified, is optionally substituted by $C_1$-$C_8$-alkyl, halogen, $C_1$-$C_8$-alkoxy, carboxy, $C_1$-$C_8$-alkyl-carboxy, $C_1$-$C_8$-haloalkyl, $C_1$-$C_8$-haloalkoxy, $C_3$-$C_{15}$-carbocyclic group, $C_1$-$C_8$-alkylcarbonyl, $C_1$-$C_8$-alkoxycarbonyl, nitro, cyano, R$^{15}$, a $C_1$-$C_8$-alkyl substituted by R$^{15}$, R$^{16}$ or a $C_1$-$C_8$-alkyl substituted by R$^{16}$;

each R$^{11}$ and R$^{12}$, are independently selected from H, $C_1$-$C_8$-alkyl, $C_1$-$C_8$-haloalkyl, $C_3$-$C_{15}$-carbocyclic group, $C_6$-$C_{15}$-aromatic carbocyclic group and a 4- to 14-membered heterocyclic group optionally substituted by —COOH or $C_1$-$C_8$-alkyl, or R$^{11}$ and R$^{12}$, together with the nitrogen they are attached, form a 5- to 14-membered heterocyclic group optionally substituted by CO$_2$H, $C_1$-$C_8$-alkyl, (C═O)-4- to 14-membered heterocyclic group or a $C_6$-$C_{15}$-membered aromatic carbocyclic group, when R$^{11}$ or R$^{12}$ are $C_1$-$C_8$-alkyl they may be optionally mono- or di-substituted by $C_6$-$C_{15}$-aromatic carbocyclic group, 5- to 14-membered heterocyclic group, $C_1$-$C_8$-alkylamino optionally substituted by OH or a di($C_1$-$C_8$-alkyl)amino optionally substituted by OH;

$R^{11a}$ is selected from H and $C_1$-$C_8$-alkyl; and $R^{14}$ is selected from H, halogen, $C_1$-$C_8$-alkyl, OH, $C_6$-$C_{15}$-membered aromatic carbocyclic group, $C_7$-$C_{14}$-aralkyl, and O—$C_7$-$C_{14}$-aralkyl.

DEFINITIONS

Terms used in the specification have the following meanings:

"Optionally substituted" means the group referred to can be substituted at one or more positions by any one or any combination of the radicals listed thereafter.

"Halo" or "halogen", as used herein, may be fluorine, chlorine, bromine or iodine.

"$C_1$-$C_8$-Alkyl", as used herein, denotes straight chain or branched alkyl having 1-8 carbon atoms.

"$C_1$-$C_8$-Alkoxy", as used herein, denotes straight chain or branched alkoxy having 1-8 carbon atoms.

The term "alkylene" denotes a straight chain or branched saturated hydrocarbon chain.

The term "alkenylene" denotes a straight chain or branched partially unsaturated hydrocarbon chain containing one or more carbon-carbon double bonds.

"Amino-$C_1$-$C_8$-alkyl" and "amino-$C_1$-$C_8$-alkoxy" denote amino attached by a nitrogen atom to $C_1$-$C_8$-alkyl, e.g., $NH_2$—($C_1$-$C_8$)—, or to $C_1$-$C_8$-alkoxy, e.g., $NH_2$—($C_1$-$C_8$)—O—.

"$C_1$-$C_8$-Alkylamino" and "di($C_1$-$C_8$-alkyl)amino" denote $C_1$-$C_8$-alkyl, as hereinbefore defined, attached by a carbon atom to an amino group. The $C_1$-$C_8$-alkyl groups in di($C_1$-$C_8$-alkyl)amino may be the same or different.

"Amino-(hydroxy)-$C_1$-$C_8$-alkyl" denotes amino attached by a nitrogen atom to $C_1$-$C_8$-alkyl and hydroxy attached by an oxygen atom to the same $C_1$-$C_8$-alkyl.

"$C_1$-$C_8$-Alkylcarbonyl" and "$C_1$-$C_8$-alkoxycarbonyl", as used herein, denote $C_1$-$C_8$-alkyl or $C_1$-$C_8$-alkoxy, respectively, as hereinbefore defined, attached by a carbon atom to a carbonyl group.

"$C_3$-$C_8$-Cycloalkylcarbonyl", as used herein, denotes $C_3$-$C_8$-cycloalkyl, as hereinbefore defined, attached by a carbon atom to a carbonyl group.

"$C_7$-$C_{14}$-Aralkyl", as used herein, denotes alkyl, e.g., $C_1$-$C_4$-alkyl, as hereinbefore defined, substituted by a $C_6$-$C_{10}$-aromatic carbocyclic group, as herein defined.

"$C_3$-$C_{15}$-Carbocyclic group", as used herein, denotes a carbocyclic group having 3- to 15-ring carbon atoms that is saturated or partially saturated, such as a $C_3$-$C_8$-cycloalkyl. Examples of $C_3$-$C_{15}$-carbocyclic groups include but are not limited to cyclopropyl, cyclobutyl, cyclopentyl, cyclohexyl, cycloheptyl or cyclooctyl or a bicyclic group, such as bicyclooctyl, bicyclononyl including indanyl and indenyl and bicyclodecyl.

"$C_6$-$C_{15}$-Aromatic carbocyclic group", as used herein, denotes an aromatic group having 6- to 15-ring carbon atoms. Examples of $C_6$-$C_{15}$-aromatic carbocyclic groups include, but are not limited to, phenyl, phenylene, benzenetriyl, naphthyl, naphthylene, naphthalenetriyl or anthrylene.

"4- to 8-Membered heterocyclic group", "3- to 14-membered heterocyclic group", "4- to 14-membered heterocyclic group" and "5- to 14-membered heterocyclic group", refers, respectively, to 4- to 8-membered, 3- to 14-membered, 4- to 14-membered and 5- to 14-membered heterocyclic rings containing at least one ring heteroatom selected from the group consisting of nitrogen, oxygen and sulphur, which may be saturated, partially saturated or unsaturated (aromatic). Examples of such heterocyclic groups include, but are not limited to, furan, pyrrole, pyrrolidine, pyrazole, imidazole, triazole, isotriazole, tetrazole, thiadiazole, isothiazole, oxadiazole, pyridine, piperidine, pyrazine, oxazole, isoxazole, pyrazine, pyridazine, pyrimidine, piperazine, pyrrolidine, pyrrolidinone, morpholine, triazine, oxazine, tetrahydrofuran, tetrahydrothiophene, tetrahydrothiopyran, tetrahydropyran, 1,4-dioxane, 1,4-oxathiane, indazole, quinoline, indazole, indole or thiazole.

Another embodiment of the invention provides compounds of formula (I), or tautomers, or stereoisomers, or pharmaceutically acceptable salts thereof,
wherein
$M_1$ and $M_2$ are

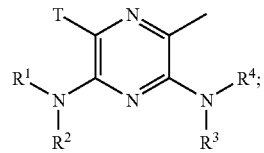

$R^1$, $R^2$, $R^3$, $R^4$, $R^5$, $R^{5a}$ and $R^6$ are H;
$L_1$ and $L_2$ are independently selected from:

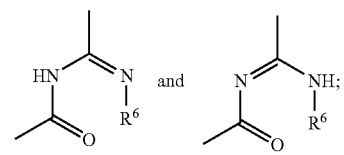

$W_1$ and $W_2$ are independently selected from $C_0$-$C_8$-alkylene;

$X_1$ and $X_2$ are independently selected from a 4- to 14-membered heterocyclic group;

$Y_1$ and $Y_2$ are independently —$C_0$-$C_8$-alkylene- or $C_1$-$C_8$alkylamino-;

A is selected from a $C_6$-$C_{15}$-membered aromatic carbocyclic group, —$CONR^{11a}$—($C_1$-$C_8$-alkylene)-$NR^{11a}CO$—, —(C=O), —CO—($C_1$-$C_8$-alkylene)-CO—, —CO—($C_1$-$C_8$-alkenylene)-CO—, —CO—($C_0$-$C_8$-alkylene)-Z—($C_0$-$C_8$-alkylene)-CO—, —$CONR^{11a}$—($C_0$-$C_8$-alkylene)-Z—($C_0$-$C_8$-alkylene)-$NR^{11a}CO$—, $C_3$-$C_{15}$-carbocyclic group and a 4- to 14-membered heterocyclic group;

Z is selected from $C_6$-$C_{15}$-membered aromatic carbocyclic group, $C_3$-$C_{15}$-carbocyclic group and a 4- to 14-membered heterocyclic group;

T is selected from H, halogen, $C_1$-$C_8$-alkyl, $C_1$-$C_8$-haloalkyl, $C_1$-$C_8$-haloalkoxy, $C_3$-$C_{15}$-carbocyclic group, nitro, cyano, a $C_6$-$C_{15}$-membered aromatic carbocyclic group, a and a $C_1$-$C_8$-alkyl substituted by a $C_6$-$C_{15}$-membered aromatic carbocyclic group;

wherein each $C_6$-$C_{15}$-membered aromatic carbocyclic group and each 4- to 14-membered heterocyclic group, unless otherwise specified is independently optionally substituted by one or more groups selected from OH, $C_1$-$C_8$-alkoxy, $C_1$-$C_8$-alkyl, halogen, $SO_2NR^{11}R^{12}$, hydroxy$C_1$-$C_8$-alkoxy, optionally substituted by hydroxyl, ($C_0$-$C_4$-alkylene) $CONR^{11}R^{12}$, ($C_0$-$C_4$-alkylene) $N=C(NR^{11}R^{12})_2$, —O—($C_1$-$C_4$-alkylene)-N=C (NR$^{11}$R$^{12}$)$_2$, —O—(C$_1$-C$_4$-alkylene)-CONR$^{11}$R$^{12}$, C$_7$-C$_{10}$-aralkoxy, C$_7$-C$_{10}$-aralkyl, SH, S(C$_1$-C$_8$-alkylene), SO$_2$(C$_1$-C$_8$-alkylene) SO(C$_1$-C$_8$-alkylene), NR$^{11}$R$^{12}$, NR$^{11}$(C$_3$-C$_{12}$-carbocyclic group) where the carbocyclic group is optionally substituted by halogen or C$_1$-C$_8$-alkyl, R$^{15}$, a C$_1$-C$_8$-alkyl substituted by R$^{15}$, R$^{16}$, a C$_1$-C$_8$-alkyl substituted by R$^{16}$, O(C$_1$-C$_8$-alkylene)-NR$^{11}$C(C=O)O—(C$_0$-C$_4$-alkylene)-R$^{15}$, cyano, oxo, carboxy, nitro, C$_1$-C$_8$-alkylcarbonyl, hydroxy-C$_1$-C$_8$-alkyl, C$_1$-C$_8$-haloalkyl, amino-C$_1$-C$_6$-alkyl, amino (hydroxy)C$_1$-C$_8$-alkyl and C$_1$-C$_8$-alkoxy optionally substituted by aminocarbonyl, where R$^{15}$ is a C$_6$-C$_{15}$-membered aromatic carbocyclic group, optionally substituted by OH, C$_1$-C$_8$-alkoxy, C$_1$-C$_8$-alkyl, halogen and C$_1$-C$_8$-haloalkyl, R$^{16}$ is a 3- to 14-membered heterocyclic group, optionally substituted by OH, C$_1$-C$_8$-alkoxy, C$_1$-C$_8$-alkyl, C$_6$-C$_{15}$-membered aromatic carbocyclic group, CO$_2$H, (C=O)-3- to 14-membered heterocyclic group, halogen and C$_1$-C$_8$-haloalkyl;

each R$^{11}$ and R$^{12}$, are independently selected from H, C$_1$-C$_8$-alkyl, C$_3$-C$_{15}$-carbocyclic group, C$_6$-C$_{15}$-aromatic carbocyclic group, or R$^{11}$ and R$^{12}$, together with the nitrogen they are attached, form a 4- to 8-membered heterocyclic group optionally substituted by CO$_2$H, C$_1$-C$_4$-alkyl, (C=O)-4- to 8-membered heterocyclic group or a C$_6$-C$_{10}$-membered aromatic carbocyclic group, when R$^{11}$ or R$^{12}$ are C$_1$-C$_8$-alkyl they may be optionally mono- or di-substituted by C$_6$-C$_{10}$-aromatic carbocyclic group, C$_3$-C$_8$-membered heterocyclic group, or a di(C$_1$-C$_8$-alkyl)amino optionally substituted by OH; and R$^{11a}$ is selected from H and C$_1$-C$_8$-alkyl.

In compounds of formula (I), the following meanings are preferred independently, collectively or in any combination:

According to formula (I), L$_1$ and L$_2$ are suitably

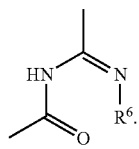

Equally suitably, L$_1$ and L$_2$ are

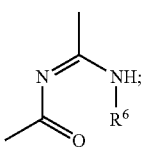

According to formula (I), R$^1$ is suitably H.
According to formula (I), R$^2$ is suitably H.
According to formula (I), R$^3$ is suitably H.
According to formula (I), R$^4$ is suitably H.
M$_1$, and M$_2$ are suitably

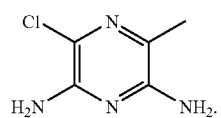

According to formula (I), W$_1$ and W$_2$ are suitably C$_0$ alkylene.

According to formula (I), X$_1$ and X$_2$ are suitably piperidine.

According to formula (I), Y$_1$ and Y$_2$ are suitably C$_0$ alkylene.

According to formula (I), suitably R$^5$ and R$^{5a}$ are H.

According to formula (I), R$^6$ is suitably H.

A is suitably selected from a C$_6$-C$_{15}$-membered aromatic carbocyclic group, —CONH—(C$_1$-C$_8$-alkylene)-NHCO—, —CO—(C$_1$-C$_8$-alkylene)-CO—, —CO—(C$_1$-C$_8$-alkenylene)-CO—, —(C=O), —CO—(C$_0$-C$_8$-alkylene)-Z—(C$_0$-C$_8$-alkylene)-CO—, —CONH—(C$_0$-C$_8$-alkylene)-Z—(C$_0$-C$_7$-alkylene)-NHCO—, C$_3$-C$_{15}$-carbocyclic group and a 4- to 14-membered heterocyclic group, e.g.,

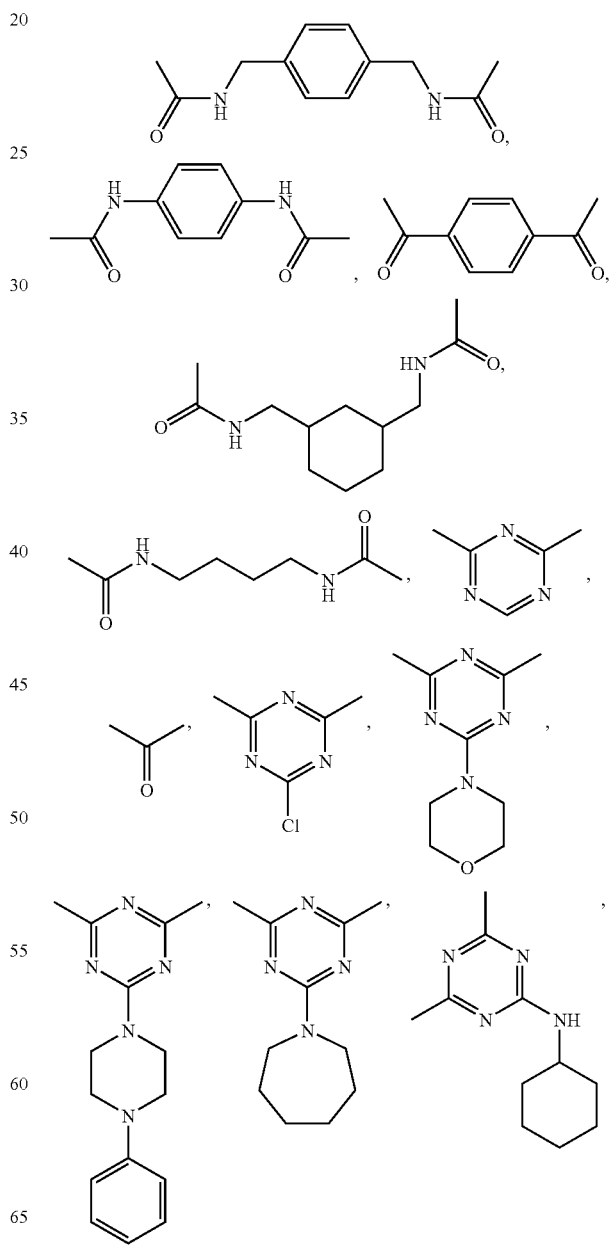

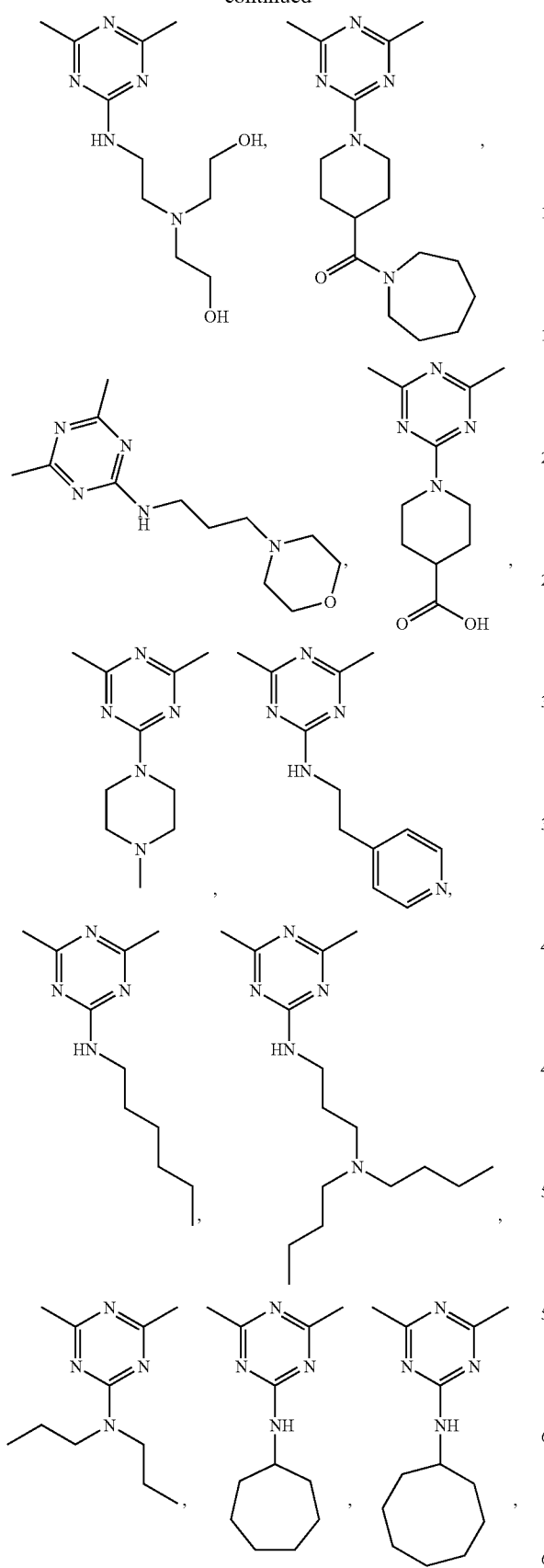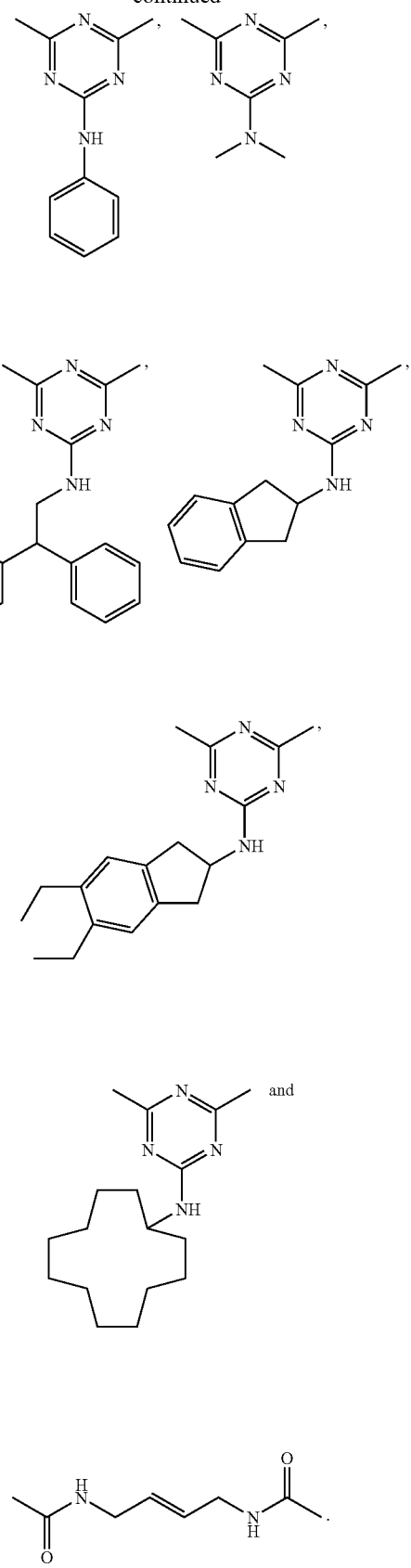

Another aspect of the present invention provides compounds of formula (Ia):
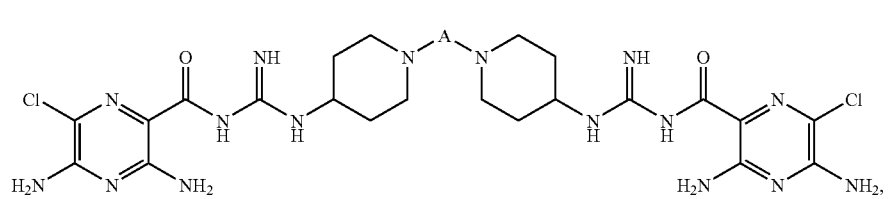
or tautomers, or stereoisomers, or pharmaceutically acceptable salts thereof,
wherein A is selected from:
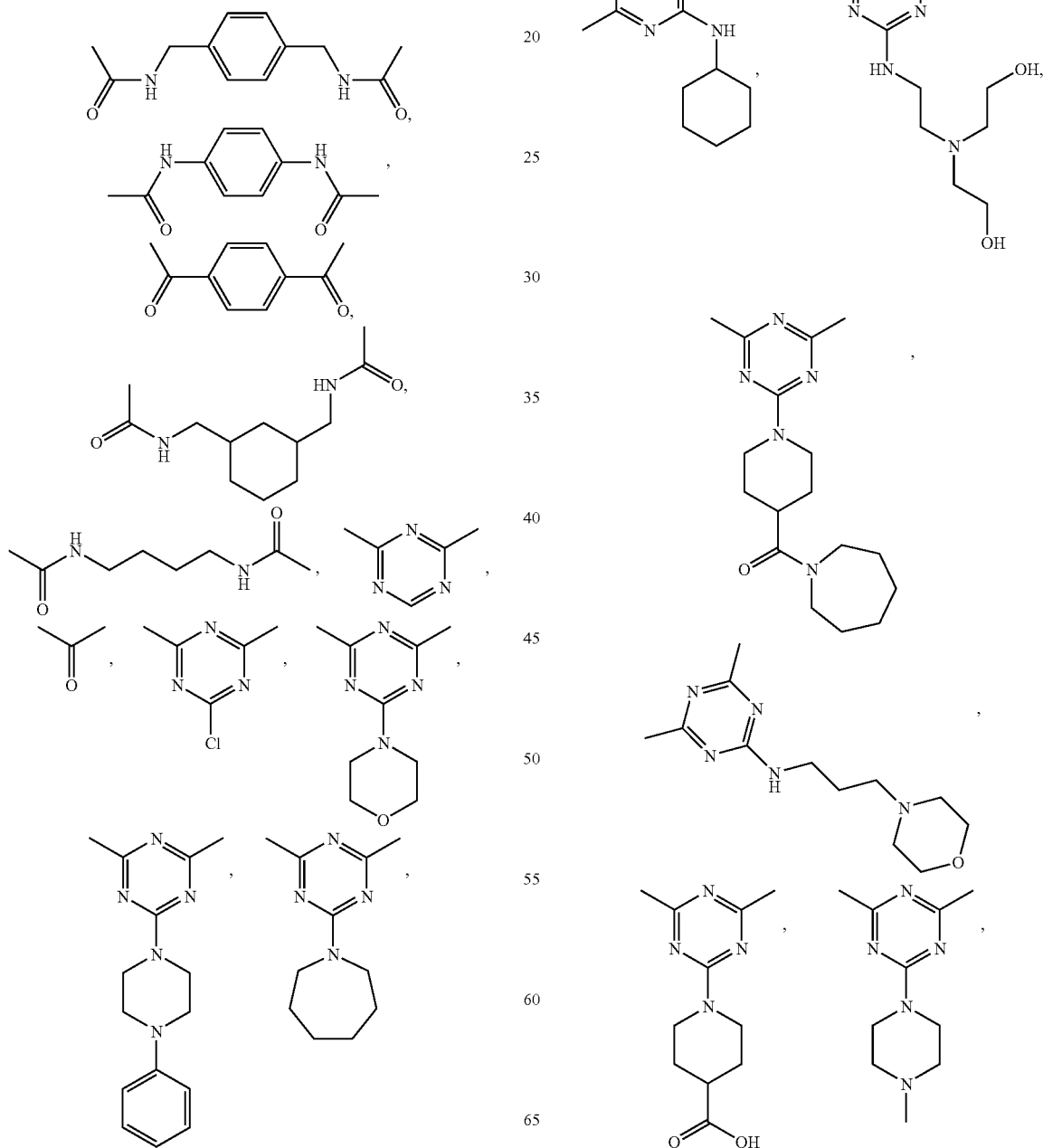

In another embodiment, the present invention provides for the use of a compound of formula (I) in any of the aforementioned embodiments, in free or pharmaceutically acceptable salt form, for the manufacture of a medicament for the treatment of an inflammatory or allergic condition, particularly an inflammatory or obstructive airways disease or mucosal hydration.

A preferred embodiment of the present invention provides for the use of a compound of formula (I) in any of the aforementioned embodiments, in free or pharmaceutically acceptable salt form, for the manufacture of a medicament for the treatment of an inflammatory or allergic condition selected from cystic fibrosis, primary ciliary dyskinesia, chronic bronchitis, chronic obstructive pulmonary disease, asthma, respiratory tract infections, lung carcinoma, xerostomia and keratoconjunctivitis.

It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments. It is understood by those skilled in the art that combinations of substituents where not possible are not an aspect of the present invention.

Throughout this specification and in the claims that follow, unless the context requires otherwise, the word "comprise", or variations, such as "comprises" or "comprising", will be understood to imply the inclusion of a stated integer or step or group of integers or steps but not the exclusion of any other integer or step or group of integers or steps.

Especially preferred specific compounds of formula (I) are those described hereinafter in the Examples.

The compounds represented by formula (I) may be capable of forming acid addition salts, particularly pharmaceutically acceptable acid addition salts. Pharmaceutically acceptable acid addition salts of the compound of formula (I) include those of inorganic acids, e.g., hydrohalic acids, such as hydrofluoric acid, hydrochloric acid, hydrobromic acid or hydroiodic acid, nitric acid, sulfuric acid, phosphoric acid; and organic acids, e.g., aliphatic monocarboxylic acids, such as formic acid, acetic acid, trifluoroacetic acid, propionic acid and butyric acid; aliphatic hydroxy acids, such as lactic acid, citric acid, tartaric acid or malic acid; dicarboxylic acids, such as maleic acid or succinic acid; aromatic carboxylic acids, such as benzoic acid, p-chlorobenzoic acid, diphenylacetic acid, para-biphenyl benzoic acid or triphenylacetic acid; aromatic hydroxy acids, such as o-hydroxybenzoic acid, p-hydroxybenzoic acid, 1-hydroxynaphthalene-2-carboxylic acid or 3-hydroxynaphthalene-2-carboxylic acid; cinnamic acids, such as 3-(2-naphthalenyl)propenoic acid, para-methoxy cinnamic acid or para-methyl cinnamic acid; and sulfonic acids, such as methanesulfonic acid or benzenesulfonic acid. These salts may be prepared from compounds of formula (I) by known salt-forming procedures.

Compounds of formula (I) which may contain acidic, e.g., carboxyl, groups, are also capable of forming salts with bases, in particular, pharmaceutically acceptable bases, such as those well-known in the art; suitable such salts include metal salts, particularly alkali metal or alkaline earth metal salts, such as sodium, potassium, magnesium or calcium salts; or salts with ammonia or pharmaceutically acceptable organic amines or heterocyclic bases, such as ethanolamines, benzylamines or pyridine. These salts may be prepared from compounds of formula (I) by known salt-forming procedures.

Pharmaceutically acceptable solvates in accordance with the invention include those wherein the solvent of crystallisation may be isotopically substituted e.g. $D_2O$, $d_6$-acetone or $d_6$-DMSO.

Compounds of formula I in free form may be converted into salt form, and vice versa, in a conventional manner. The compounds in free or salt form can be obtained in the form of hydrates or solvates containing a solvent used for crystallisation. Compounds of formula I can be recovered from reaction mixtures and purified in a conventional manner. Isomers, such as enantiomers, may be obtained in a conventional manner, e.g. by fractional crystallisation or asymmetric synthesis from correspondingly asymmetrically substituted, e.g. optically active, starting materials.

Some compounds of the invention contain at least one asymmetric carbon atom and thus they exist in individual optically active isomeric forms or as mixtures thereof, e.g. as racemic mixtures. In cases where additional asymmetric centres exist the present invention also embraces both individual optically active isomers as well as mixtures, e.g. diastereomeric mixtures, thereof.

The invention includes all such forms, in particular the pure isomeric forms. The different isomeric forms may be separated or resolved one from the other by conventional methods, or any given isomer may be obtained by conventional synthetic methods or; by stereospecific or asymmetric syntheses. Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

The invention includes all pharmaceutically acceptable isotopically-labelled compounds of formula I wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen e.g. $^2H$ and $^3H$, carbon e.g. $^{11}C$, $^{13}C$ and $^{14}C$, chlorine e.g. $^{36}Cl$, fluorine e.g. $^{18}F$, iodine e.g. $^{123}I$ and $^{125}I$, nitrogen e.g. $^{13}N$ and $^{15}N$, oxygen e.g. $^{15}O$, $^{17}O$ and $^{18}O$, and sulfur e.g. $^{35}S$.

Certain isotopically-labelled compounds of formula I, for example those incorporating a radioactive isotope, are useful in drug and/or substrate tissue distribution studies. The radioactive isotopes tritium ($^3H$) and carbon-14 ($^{14}C$) are particularly useful for this purpose in view of their ease of incorporation and ready means of detection. Substitution with heavier isotopes such as deuterium ($^2H$) may afford certain therapeutic advantages that result from greater metabolic stability, for example increased in vivo half-life or reduced dosage requirements, and hence may be preferred in some circumstances. Substitution with positron emitting isotopes, such as $^{11}C$, $^{18}F$, $^{15}O$, and $^{13}N$ can be useful in Positron Emission Topography (PET) studies for examining substrate receptor occupancy.

Isotopically-labelled compounds of formula I can generally be prepared by conventional techniques known to those skilled in the art or by processes analogous to those described in the accompanying examples using an appropriate isotopically-labelled reagent in place of the non-labelled reagent previously used.

Tautomers are one of two or more structural isomers that exist in equilibrium and are readily converted from one isomeric form to another.

Examples of tautomers include but are not limited to those described in the claims and also include compounds of formula (II):

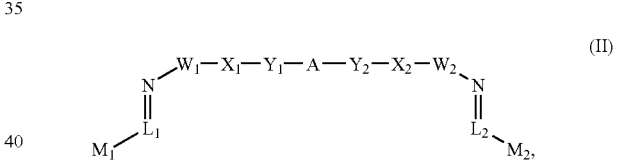

where
$M_1$, $M_2$, $W_1$, $W_2$, $X_1$, $X_2$, $Y_1$, $Y_2$ and A are as described hereinbefore; and
$L_1$ and $L_2$ are

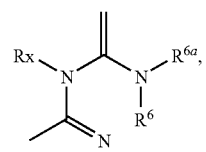

where Rx, $R^6$ and $R^{6a}$ are independently selected from H, $C_1$-$C_8$ alkyl, $C_1$-$C_8$-alkyl-carboxy, $C_1$-$C_8$-alkyl-alkoxy, $C_1$-$C_8$-haloalkyl, $C_3$-$C_{15}$-carbocyclic group, $C_1$-$C_8$-alkylcarbonyl, $C_1$-$C_8$-alkoxycarbonyl, nitro, cyano, a $C_6$-$C_{15}$-membered aromatic carbocyclic group, a 4- to 14-membered heterocyclic group, a $C_1$-$C_8$-alkyl substituted by a 4- to 14-membered heterocyclic group, and a $C_1$-$C_8$-alkyl substituted by a $C_6$-$C_{15}$-membered aromatic carbocyclic group.

The compounds of the invention may exist in both unsolvated and solvated forms. The term "solvate" is used herein to describe a molecular complex comprising the compound of the invention and one or more pharmaceutically acceptable solvent molecules, e.g., ethanol. The term "hydrate" is employed when said solvent is water.

Synthesis

An embodiment of the present invention provides a process for the preparation of compounds of formula (I):

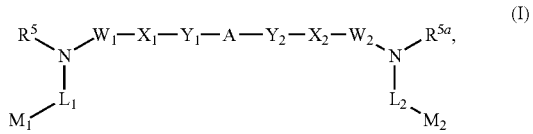

or tautomers, or stereoisomers, or pharmaceutically acceptable salts thereof,
wherein
$M_1, M_2, L_1, L_2, NR^5, NR^{5a}, W_1, W_2, X_1, X_2, Y_1, Y_2$, and A are as defined hereinbefore, which comprises the steps of:

(i) reacting a compound of formula (IV)

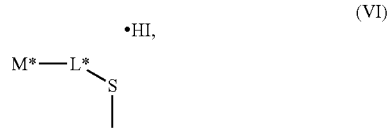

wherein
M* is $M_1$ or $M_2$;
L* is $L_1$ or $L_2$; and
$M_1, M_2, L_1, L_2$ and T are as hereinbefore defined,
with compounds of formula (V):

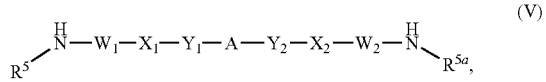

wherein $R^5, R^{5a}, W_1, W_2, X_1, X_2, Y_1, Y_2$ and A are hereinbefore defined, optionally in the presence of a base, e.g., an organic base; and in an organic solvent, e.g., a non-protic dipolar solvent; and (ii) recovering the resultant compound of formula (I), in free or pharmaceutically acceptable salt form.

The compounds of formula (I) can be prepared, e.g., using the reactions and techniques described below and in the Examples. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The various substituents on the synthetic intermediates and final products shown in the following reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of formula (I) into another compound of formula (I). Examples of such manipulations are conversion of an ester or a ketone to an alcohol; conversion of an ester to a ketone; interconversions of esters, acids and amides; alkylation, acylation and sulfonylation of alcohols and amines; and many others. Substituents can also be added using common reactions, such as alkylation, acylation, halogenation or oxidation. Such manipulations are well-known in the art, and many reference works summarize procedures and methods for such manipulations. Some reference works which gives examples and references to the primary literature of organic synthesis for many functional group manipulations, as well as other transformations commonly used in the art of organic synthesis are *March's Organic Chemistry*, 5th Edition, Wiley and Chichester, Eds. (2001); *Comprehensive Organic Transformations*, Larock, Ed., VCH (1989); *Comprehensive Organic Functional Group Transformations*, Katritzky et al. (series editors), Pergamon (1995); and *Comprehensive Organic Synthesis*, Trost and Fleming (series editors), Pergamon (1991). It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practitioner is Greene and Wuts, *Protective Groups in Organic Synthesis*, Wiley and Sons (1999).

Generally, compounds described in the scope of this patent application can be synthesized by the routes described in Scheme 1 and Scheme 2 and the Examples.

In Scheme 1, compounds of formula (Ib) can be prepared according to the processes described by Cragoe et al., *J Med Chem*, Vol. 10, pp. 66-73 (1967); and European Patent EP 0 017 152 and U.S. Pat. No. 3,544,571. For instance, intermediate 1 (R═H) can be reacted with intermediate 2, where A is as defined hereinbefore, in the presence of triethylamine in organic solvent to provide compound (Ib) as the free base. The free base can then be converted to a salt form by treatment with an appropriate acid. Alternatively the coupling reaction may be performed in the presence of a BoC or CBz protection. Intermediates can be prepared from methods known by those skilled in the art or are commercially-available.

Scheme 1

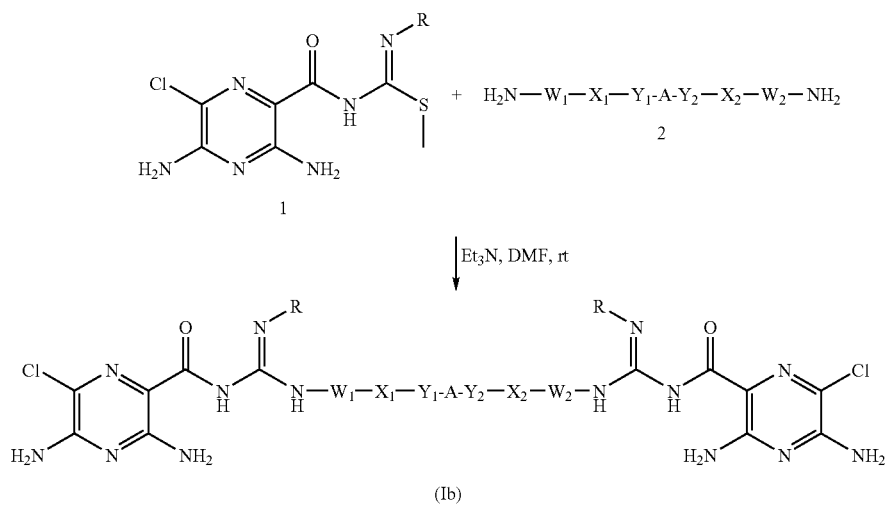

(Ib)

Where R = H or a BoC or CBz group

Compounds of formula (Ic) can also be prepared according to Scheme 2, where $Y_1$ or $X_1$ in intermediate 2 contains a primary or secondary amine protected by group P by reacting intermediate 1 with a mono protected diamine (intermediate 2) in the presence of triethylamine in organic solvent to provide intermediate 3. Subsequent deprotection of intermediate 3 using conventional deprotection techniques affords Intermediate 4. Intermediate 4 may be reacted with $AJ_1J_2(J_3)_n$ and intermediate 4a, where $Y_2$ or $X_2$ in intermediate 4a contains a primary or secondary amine, to provide compound (Ic). Where n=1, A may be additionally substituted to provide compound (Ic). A, $Y_2$, $X_2$, $W_2$, $L_2$, $R^5$, and $M_2$ are hereinbefore defined. P represents a standard amine protecting group, e.g., Boc, CBz, acetate and deprotection is by standard means. $J_1$, $J_2$ and $J_3$ in conjunction with group A independently provide functionality capable of reacting with amines, e.g., halogen, thioether, carboxylic acid, isocyanate, sulfonyl chlorides, aldehydes and ketones. In either case intermediate 1 may also be protected by a suitable N protecting group, e.g., Boc, CBz utilising methods known in the literature and by those skilled in the art.

Scheme 2

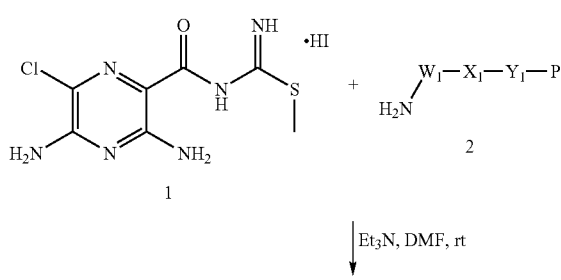

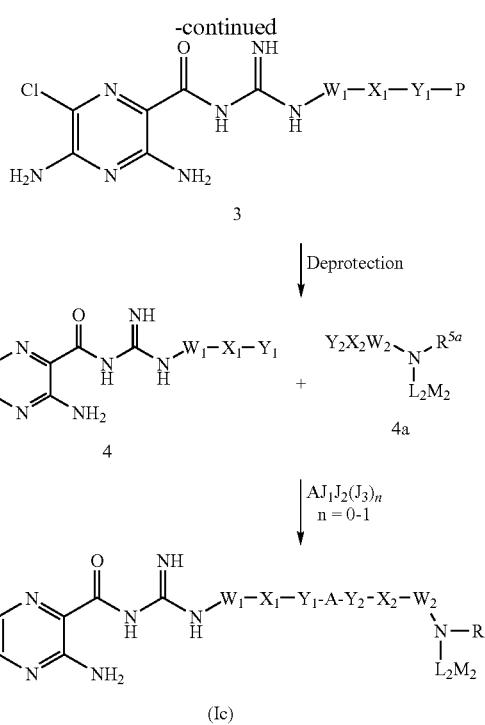

Compounds of formula (I), in free form, may be converted into salt form, and vice versa, in a conventional manners understood by those skilled in the art. The compounds in free or salt form can be obtained in the form of hydrates or solvates containing a solvent used for crystallisation. Compounds of formula (I) can be recovered from reaction mixtures and purified in a conventional manner. Isomers, such as stereoisomers, may be obtained in a conventional manner, e.g., by fractional crystallisation or asymmetric synthesis from correspondingly asymmetrically substituted, e.g., optically active, starting materials.

Pharmacological Activity

Having regard to their blockade of the epithelial sodium channel (ENaC), compounds of formula (I), in free or pharmaceutically acceptable salt form, hereinafter alternately referred to as "agents of the invention", are useful in the treatment of conditions which respond to the blockade of the epithelial sodium channel, particularly conditions benefiting from mucosal hydration.

Diseases treatable by blockade of the epithelial sodium channel, include diseases associated with the regulation of fluid volumes across epithelial membranes. For example, the volume of airway surface liquid is a key regulator of mucociliary clearance and the maintenance of lung health. The blockade of the epithelial sodium channel will promote fluid accumulation on the mucosal side of the airway epithelium thereby promoting mucus clearance and preventing the accumulation of mucus and sputum in respiratory tissues (including lung airways). Such diseases include respiratory diseases, such as cystic fibrosis, primary ciliary dyskinesia, chronic bronchitis, chronic obstructive pulmonary disease (COPD), asthma, respiratory tract infections (acute and chronic; viral and bacterial) and lung carcinoma. Diseases influenced by blockade of the epithelial sodium channel also include diseases other than respiratory diseases that are associated with abnormal fluid regulation across an epithelium, perhaps involving abnormal physiology of the protective surface liquids on their surface, e.g., xerostomia (dry mouth) or keratoconjunctivitis sire (dry eye). Furthermore, blockade of the epithelial sodium channel in the kidney could be used to promote diuresis and thereby induce a hypotensive effect.

Treatment in accordance with the invention may be symptomatic or prophylactic.

Cystic fibrosis includes disease of the lung, including atypical, mild, moderate, and severe cystic fibrosis lung disease, as well as exacerbation of airways hyperreactivity consequent to other drug therapy, in particular, other inhaled drug therapy. Cystic fibrosis also includes disease of other organ systems affected by cystic fibrosis, e.g., the nasal sinuses, gastrointestinal tract, and reproductive tract.

Chronic obstructive pulmonary disease includes chronic bronchitis or dyspnea associated therewith, emphysema, as well as exacerbation of airways hyperreactivity consequent to other drug therapy, in particular, other inhaled drug therapy. The invention is also applicable to the treatment of bronchitis of whatever type or genesis including, e.g., acute, arachidic, catarrhal, croupus, chronic or phthinoid bronchitis.

Asthma includes both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g., of acute asthmatic or bronchoconstrictor attack, improvement in lung function or improved airways hyperreactivity. It may further be evidenced by reduced requirement for other, symptomatic therapy, i.e., therapy for or intended to restrict or abort symptomatic attack when it occurs, e.g., anti-inflammatory (e.g., corticosteroid) or bronchodilatory. Prophylactic benefit in asthma may, in particular, be apparent in subjects prone to "morning dipping". "Morning dipping" is a recognized asthmatic syndrome, common to a substantial percentage of asthmatics and characterized by asthma attack, e.g., between the hours of about 4-6 am, i.e., at a time normally substantially distant from any previously administered symptomatic asthma therapy.

The suitability of epithelial sodium channel blocker as a treatment of a disease benefiting from mucosal hydration, may be tested by determining the inhibitory effect of the channel blocker on ENaC in a suitable cell-based assay. For example single cells or confluent epithelia, endogenously expressing or engineered to overexpress ENaC can be used to assess channel function using electrophysiological techniques or ion flux studies. See methods described in: Hirsh et al., *J Pharm Exp Ther* (2004); Moody et al., *Am J Physiol Cell Physiol* (2005).

Epithelial sodium channel blockers, including the compounds of formula (I), are also useful as co-therapeutic agents for use in combination with other drug substances, such as anti-inflammatory, bronchodilatory, anti-infective, chloride-secretagogue, alternative mucokinetic, antihistamine or antitussive drug substances, particularly in the treatment of cystic fibrosis, asthma or obstructive or inflammatory airways diseases such as those mentioned hereinbefore, e.g., as potentiators of therapeutic activity of such drugs or as a means of reducing required dosaging or potential side effects of such drugs.

The epithelial sodium channel blocker may be mixed with the other drug substance in a fixed pharmaceutical composition or it may be administered separately, before, simultaneously with or after the other drug substance.

Accordingly, the invention includes as a further aspect a combination of epithelial sodium channel blocker with inhaled osmotic agents (e.g. hypertonic saline, dextran, mannitol, xylitol). Furthermore, combination with modifiers of the function of the Cystic Fibrosis Transmembrane Conductance Regulator (CFTR) are included in the invention. CFTR includes normal or "wild-type" CFTR and also mutated CFTR (e.g. $^{\Delta F508}$CFTR, $^{G551D}$CFTR). Modifiers of CFTR function refer to both potentiators of CFTR channel function and also compounds that correct the misfolding and trafficking defect observed with Class 3 mutations of CFTR e.g., those described in WO 2007/021982, WO 2006/099256, WO 2006/127588, WO 2004/080972, WO 2005/026137, WO 2005/035514, WO 2005/075435, WO 2004/111014, WO 2006/101740, WO 2004/110352, WO 2005/120497 and US 2005/0176761.

In addition, combination with suitable mucokinetic agents with distinct modes of action such as purinergic P2-receptor agonists (e.g. INS 37217), activators of alternative chloride channels (e.g. Moli-1901 [duramycin], SPI-8811), activators of a basolateral potassium conductance such as HiK1 (e.g. EBIO, DCEBIO) are included in this invention.

Combination with suitable anti-infective agents such as macrolide antibiotics (e.g. tobramycin, azithromycin) an anti-inflammatory, bronchodilatory, antihistamine, anti-tussive, antibiotic or DNase drug substance, said epithelial sodium channel blocker and said drug substance being in the same or different pharmaceutical composition. Suitable DNase drug substances include dornase alfa (Pulmozyme™), a highly-purified solution of recombinant human deoxyribonuclease I (rhDNase), which selectively cleaves DNA. Dornase alfa is used to treat cystic fibrosis.

Other useful combinations of epithelial sodium channel blockers with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D; Takeda antagonists, such as N-[[4-[[[6,7-dihydro-2-(4-methyl-phenyl)-5H-benzo-cyclohepten-8-yl]carbonyl]amino]phenyl]-methyl] tetrahydro-N,N-dimethyl-2H-pyran-4-amin-ium chloride (TAK-770); and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable anti-inflammatory drugs include steroids, in particular, glucocorticosteroids, such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists, such as montelukast and zafirlukast; PDE4 inhibitors, such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; adenosine A2B receptor antagonists such as those described in WO 02/42298; and beta-2 adrenoceptor agonists, such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula (I) of WO 0075114, which document is incorporated herein by reference, preferably compounds of the Examples thereof, especially a compound of formula:

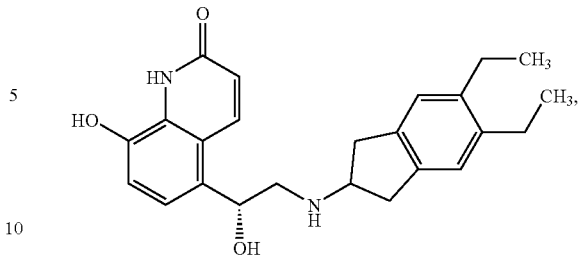

corresponding to indacaterol and pharmaceutically acceptable salts thereof, as well as compounds (in free or salt or solvate form) of formula (I) of WO 04/16601, and also compounds of EP 1440966, JP 05025045, WO 93/18007, WO 99/64035, USP 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618, WO 04/46083, WO 04/80964, WO 04/108765 and WO 04/108676.

Suitable bronchodilatory drugs include anticholinergic or antimuscarinic agents, in particular, ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285.

Suitable dual anti-inflammatory and bronchodilatory drugs include dual beta-2 adrenoceptor agonist/muscarinic antagonists such as those disclosed in USP 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841.

In accordance with the foregoing, the invention also provides as a further aspect a method for the treatment of a condition responsive to blockade of the epithelial sodium channel, e.g., diseases associated with the regulation of fluid volumes across epithelial membranes, particularly an obstructive airways disease, which comprises administering to a subject, particularly a human subject, in need thereof a compound of formula (I), in free form or in the form of a pharmaceutically acceptable salt.

In another aspect the invention provides a compound of formula (I), in free form or in the form of a pharmaceutically acceptable salt, for use in the manufacture of a medicament for the treatment of a condition responsive to blockade of the epithelial sodium channel, particularly an obstructive airways disease, e.g., cystic fibrosis and COPD.

The agents of the invention may be administered by any appropriate route, e.g. orally, e.g., in the form of a tablet or capsule; parenterally, e.g., intravenously; by inhalation, e.g., in the treatment of an obstructive airways disease; intranasally, e.g., in the treatment of allergic rhinitis; topically to the skin; or rectally. In a further aspect, the invention also provides a pharmaceutical composition comprising a compound of formula (I), in free form or in the form of a pharmaceutically acceptable salt, optionally together with a pharmaceutically acceptable diluent or carrier therefor. The composition may contain a co-therapeutic agent, such as an anti-inflammatory, broncho-dilatory, antihistamine or anti-tussive drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g., patches. Compositions for inhalation may comprise aerosol or other atomizable formulations or dry powder formulations.

When the composition comprises an aerosol formulation, it preferably contains, e.g., a hydro-fluoro-alkane (HFA) propellant, such as HFA134a or HFA227 or a mixture of these, and may contain one or more co-solvents known in the art, such as ethanol (up to 20% by weight), and/or one or more surfactants, such as oleic acid or sorbitan trioleate, and/or one or more bulking agents, such as lactose. When the composition comprises a dry powder formulation, it preferably contains, e.g., the compound of formula (I) having a particle diameter up to 10 microns, optionally together with a diluent or carrier, such as lactose, of the desired particle size distribution and a compound that helps to protect against product performance deterioration due to moisture, e.g., magnesium stearate. When the composition comprises a nebulised formulation, it preferably contains, e.g., the compound of formula (I) either dissolved, or suspended, in a vehicle containing water, a co-solvent, such as ethanol or propylene glycol and a stabilizer, which may be a surfactant.

Further aspects of the invention include:

(a) a compound of formula (I) in inhalable form, e.g., in an aerosol or other atomisable composition or in inhalable particulate, e.g., micronised form;

(b) an inhalable medicament comprising a compound of formula (I) in inhalable form;

(c) a pharmaceutical product comprising a compound of formula (I) in inhalable form in association with an inhalation device; and (d) an inhalation device containing a compound of formula I in inhalable form.

Dosages of compounds of formula (I) employed in practising the present invention will of course vary depending, e.g., on the particular condition to be treated, the effect desired and the mode of administration. In general, suitable daily dosages for administration by inhalation are of the order of 0.005-10 mg, while for oral administration suitable daily doses are of the order of 0.05-100 mg.

Pharmaceutical Use and Assay

Compounds of formula (I) and their pharmaceutically acceptable salts, hereinafter referred to alternatively as "agents of the invention", are useful as pharmaceuticals. In particular, the compounds have good ENaC blocker activity and may be tested in the following assays.

Cell Culture

Human Bronchial Epithelial cells (HBECs) (Cambrex) were cultured under air-liquid interface conditions to provide a well differentiated mucociliary phenotype.

HBECs were cultured using a modification of the method described by Gray and colleagues (Gray et al., 1996). Cells were seeded in plastic T-162 flasks and were grown in bronchial epithelial cell growth medium (BEGM; Cambrex) supplemented with bovine pituitary extract (52 µg/ml), hydrocortisone (0.5 µg/ml), human recombinant epidermal growth factor (0.5 ng/ml), epinephrine (0.5 µg/ml), transferrin (10 µg/ml), insulin (5 µg/ml), retinoic acid (0.1 µg/ml), triiodothyronine (6.5 µg/ml), gentamycin (50 µg/ml) and amphotericin B (50 ng/ml). Medium was changed every 48 hours until cells were 90% confluent. Cells were then passaged and seeded ($8.25 \times 10^4$ cells/insert) on polycarbonate Snapwell inserts (Costar) in differentiation media containing 50% DMEM in BEGM with the same supplements as above but without triiodothyronine and a final retinoic acid concentration of 50 nM (all-trans retinoic acid). Cells were maintained submerged for the first 7 days in culture, after which time they were exposed to an apical air interface for the remainder of the culture period. At this time, media was changed to DMEM:F12 media containing 2% v/v Ultroser G for the remainder of culture. Amphotericin B was removed from all media 3 feeds prior to use in the Ussing Chambers. Cells were used between days 7 and 21 after establishment of the apical-air interface. At all stages of culture, cells were maintained at 37° C. in 5% $CO_2$ in an air incubator.

Short Circuit Current (ISC) Measurements

Snapwell inserts were mounted in Vertical Diffusion Chambers (Costar) and were bathed with continuously gassed Ringer solution (5% $CO_2$ in $O_2$; pH 7.4) maintained at 37° C. containing (in mM): 120 NaCl, 25 $NaHCO_3$, 3.3 $KH_2PO_4$, 0.8 $K_2HPO_4$, 1.2 $CaCl_2$, 1.2 $MgCl_2$, and 10 glucose. The solution osmolarity was between 280 and 300 mOsmol/kg $H_2O$ for all physiological salt solutions used. Cells were voltage clamped to 0 mV (model EVC4000; WPI). RT was measured by applying a 1- or 2-mV pulse at 30-s intervals and calculating RT by Ohm's law. Data were recorded using a PowerLab workstation (ADInstruments).

Test compounds were prepared as a 10 mM stock solution in DMSO (95%). Serial 3-fold dilutions were freshly prepared in an appropriate vehicle (distilled $H_2O$ or Ringers solution). The initial concentration was added to the apical chamber as a 1000× concentrate in 5 µl, resulting in a final 1× concentration the 5 ml volume of the Ussing chamber. Subsequent additions of compound were added in a 3.3 µl volume of the 1000× serially diluted stock solution. At the completion of the concentration-response experiment, amiloride (10 µM) was added into the apical chamber to enable the total amiloride-sensitive current to be measured. An amiloride control $IC_{50}$ was established at the start of each experiment.

Results are expressed as the mean % inhibition of the amiloride-sensitive ISC. Concentration-response curves were plotted and $IC_{50}$ values generated using GraphPad Prism 3.02. Cell inserts were typically run in duplicate and the $IC_{50}$ calculated on the mean % inhibition data.

Compounds of the Examples, herein below, generally have $IC_{50}$ values in the data measurements described above below 10 µM. For example, the compounds of Examples 2, 4, 7, 13 and 23 have $IC_{50}$ values of 0.0015, 0.010, 0.006, 0.001 and 0.0016 µM, respectively.

The invention is illustrated by the following Examples.

EXAMPLES
Compounds of formula (I) which are also of formula (X):
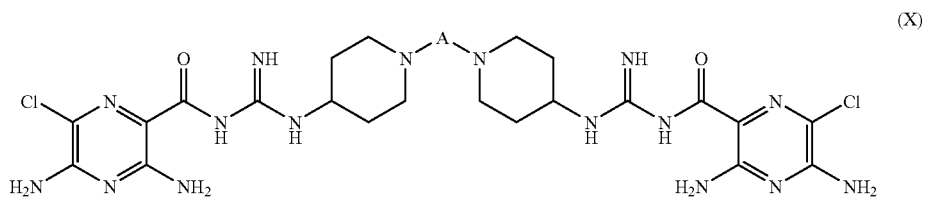
are shown in Table 1 below, the method of preparation being described hereinafter.
TABLE 1
| Ex. | Structure | M/z [M + H]+ or [M + 2H]2+ |
|---|---|---|
| 1 | 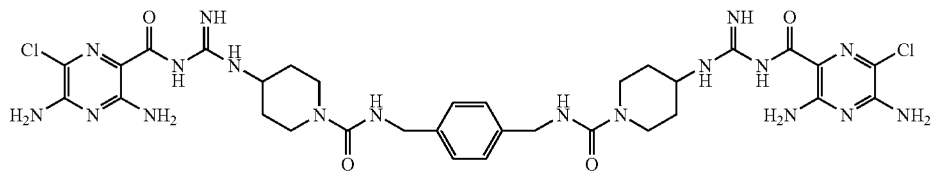 | 813 |
| 2 | 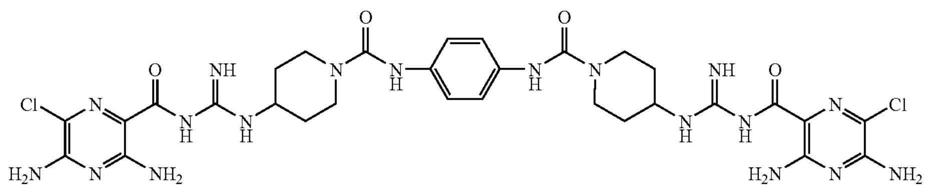 | 785 |
| 3 | 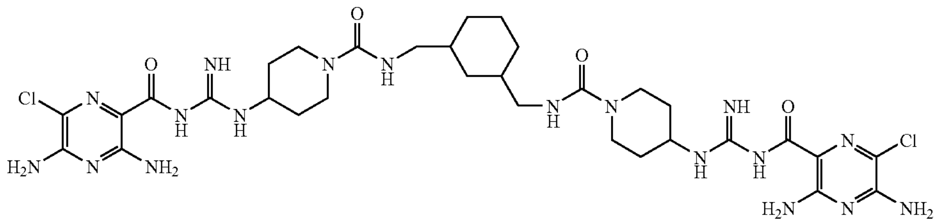 | 819 |
| 4 | 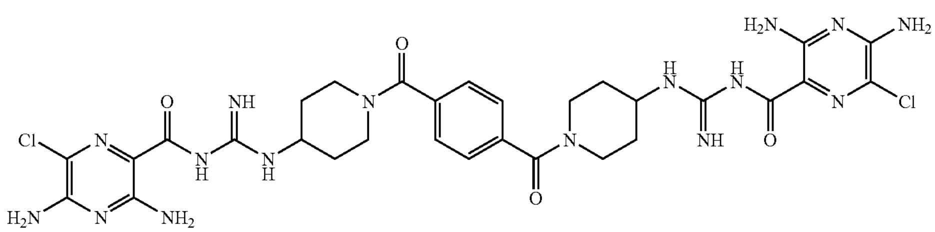 | 378 [M + 2H]2+ |
| 5 | 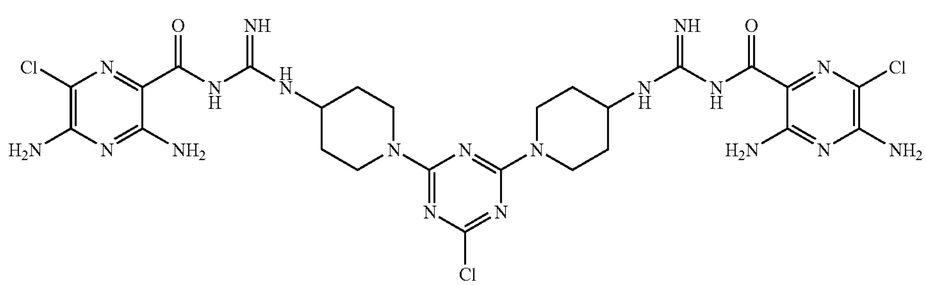 | 739 |

TABLE 1-continued

| Ex. | Structure | M/z [M + H]+ or [M + 2H]2+ |
|---|---|---|
| 6 | 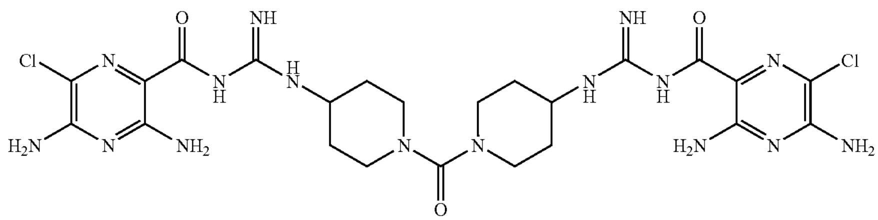 | 651 |
| 7 | 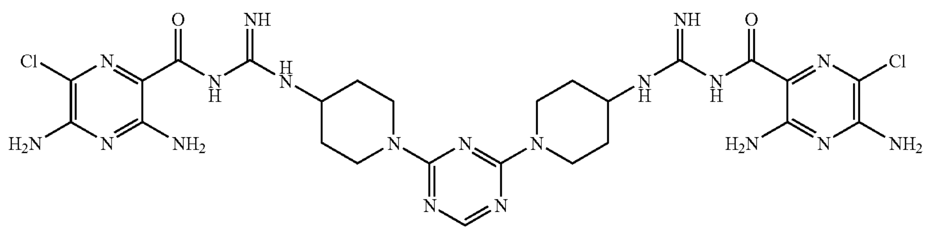 | 701 |
| 8 | 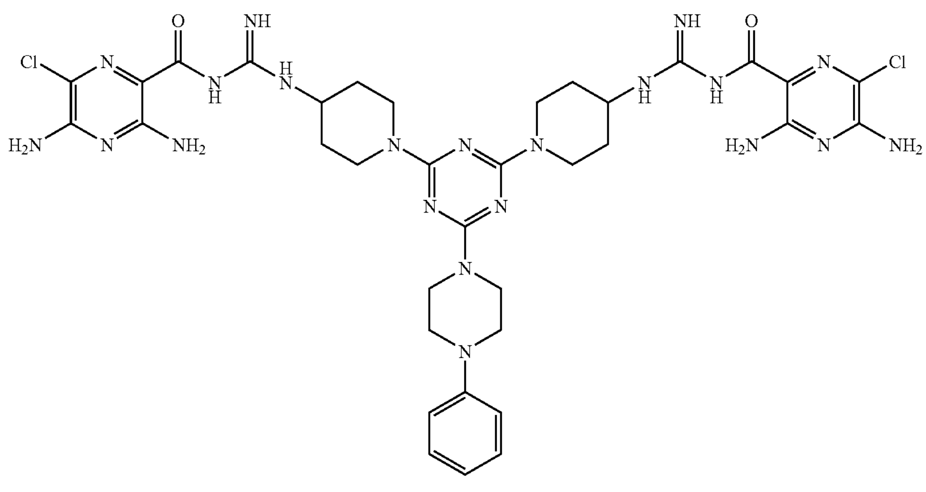 | 432 [M + 2H]2+ |
| 9 | 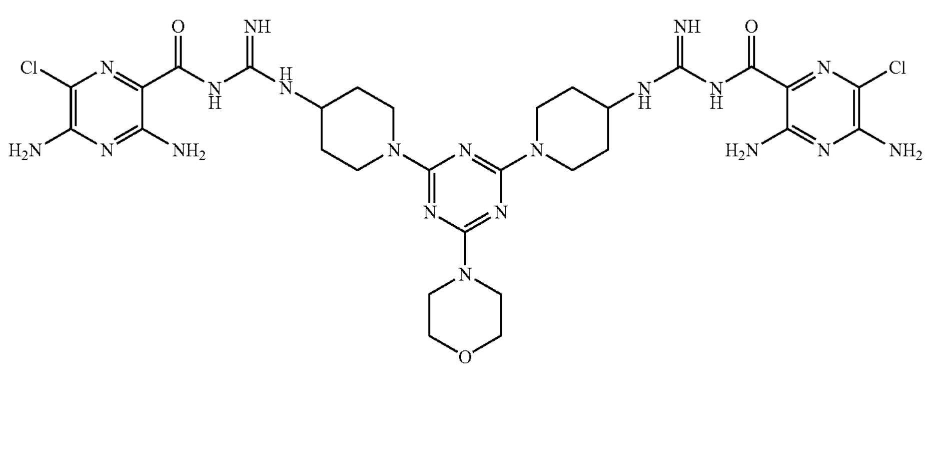 | 787 |

TABLE 1-continued
| Ex. | Structure | M/z [M + H]+ or [M + 2H]2+ |
|---|---|---|
| 10 | 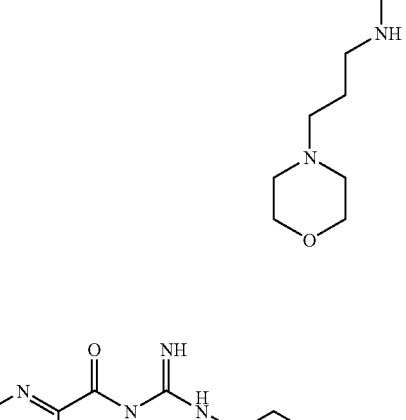 | 846 |
| 11 | 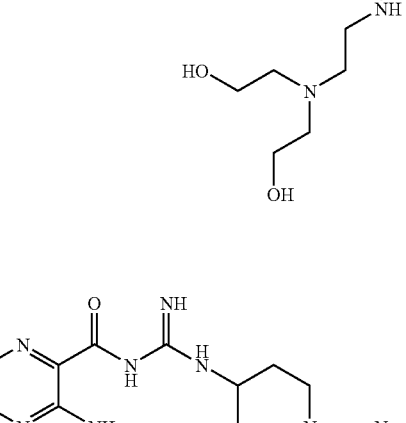 | 849 |
| 12 | 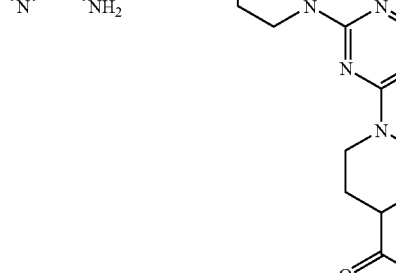 | 910 |

TABLE 1-continued

| Ex. | Structure | M/z [M + H]⁺ or [M + 2H]²⁺ |
|---|---|---|
| 13 | 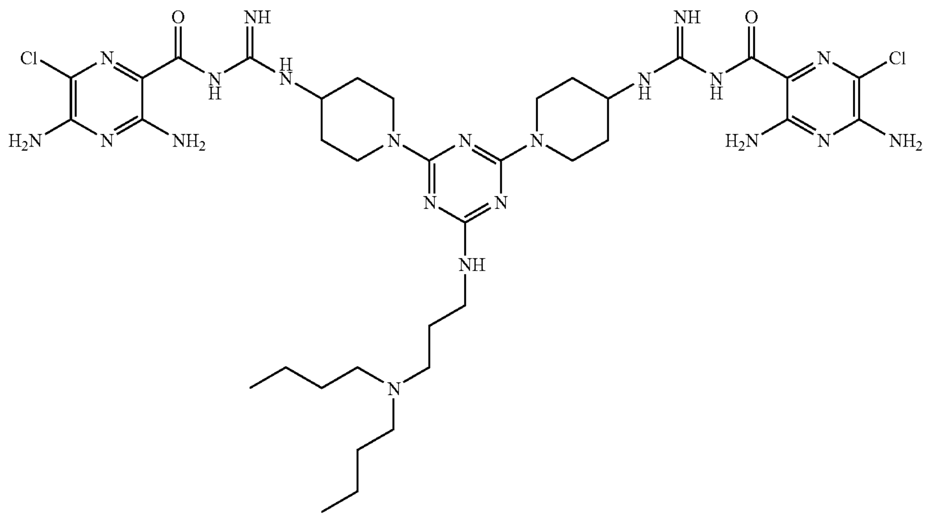 | 887 |
| 14 | 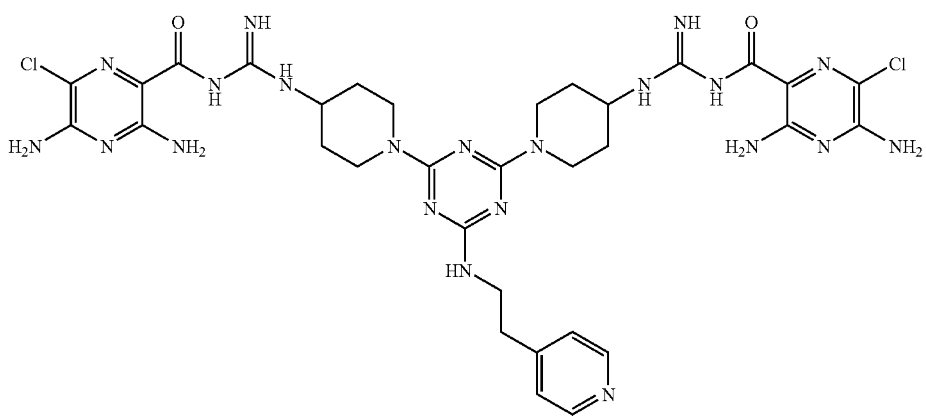 | 824 |
| 15 | 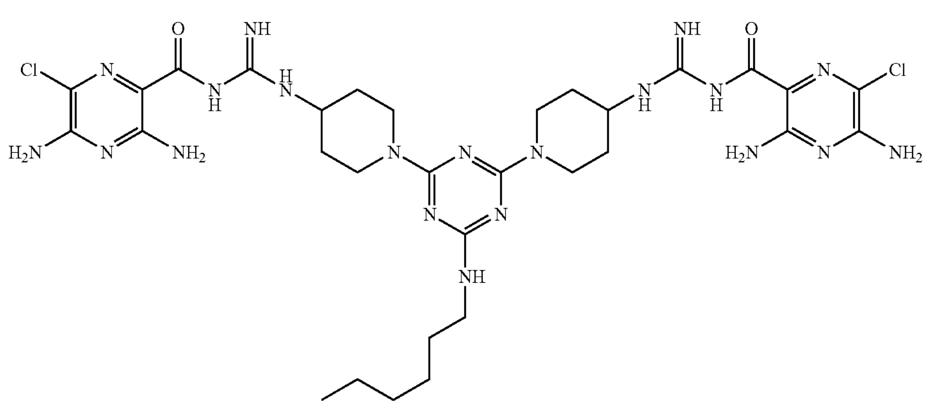 | 801 |

TABLE 1-continued

| Ex. | Structure | M/z [M + H]+ or [M + 2H]2+ |
|---|---|---|
| 16 | 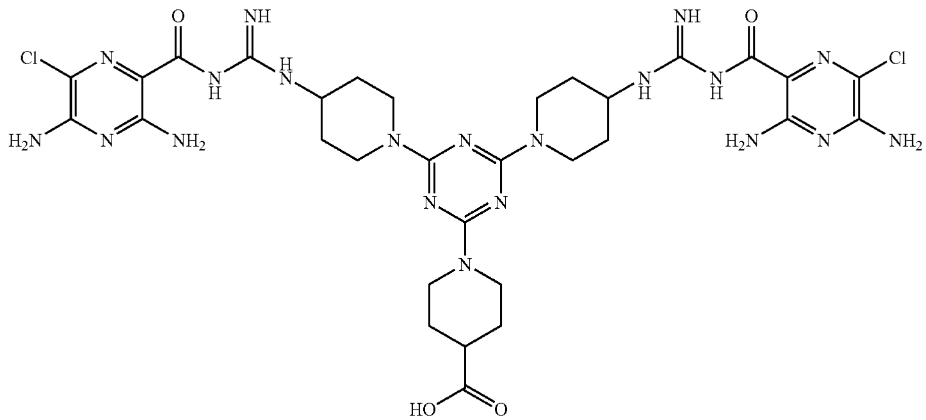 | 829 |
| 17 | 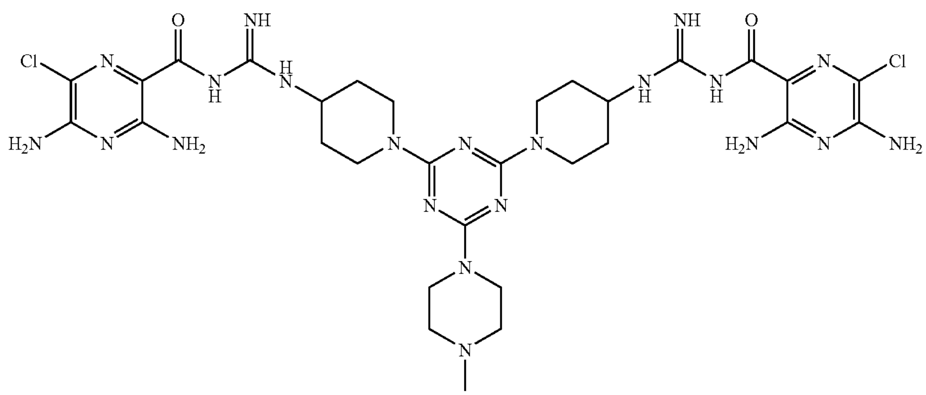 | 800 |
| 18 | 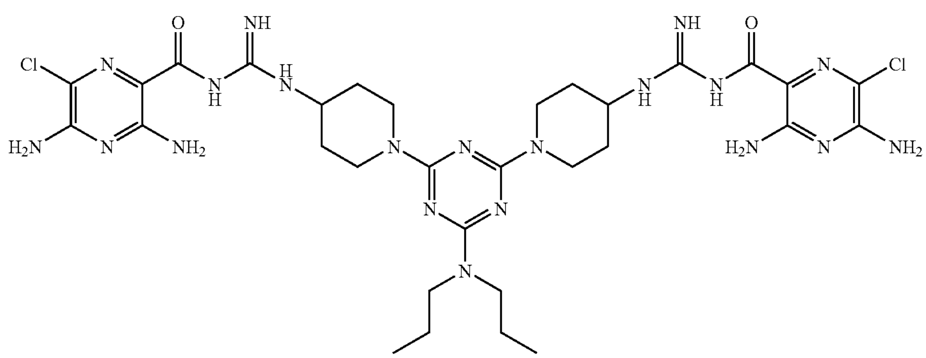 | 801 |
| 19 | 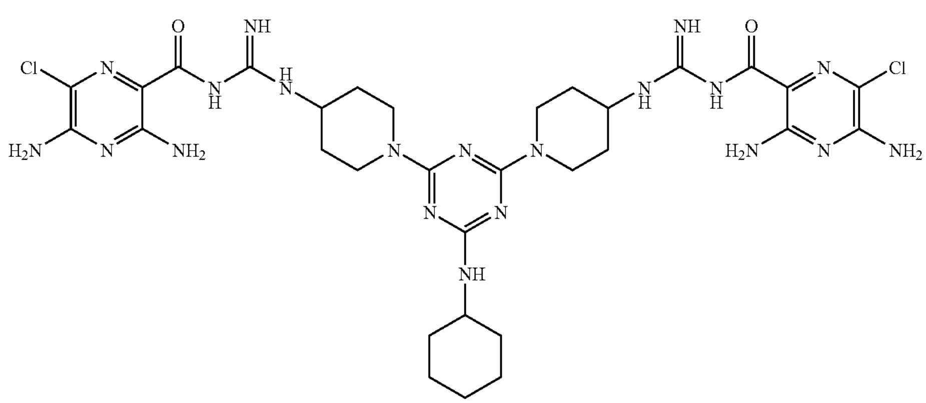 | 799 |

TABLE 1-continued
| Ex. | Structure | M/z [M + H]+ or [M + 2H]2+ |
|---|---|---|
| 20 | 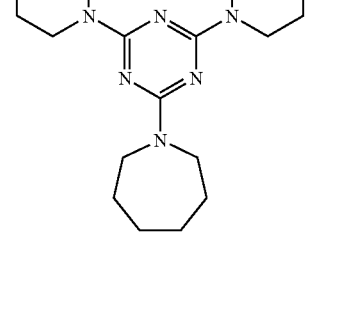 | 800 |
| 21 | 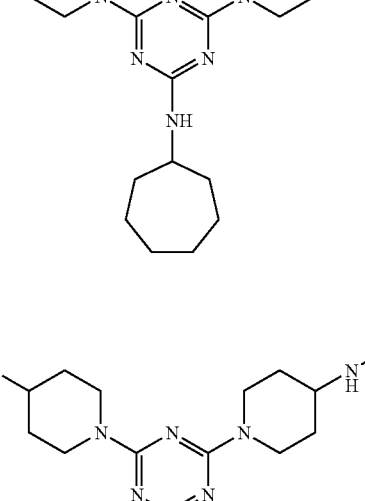 | 813 |
| 22 | 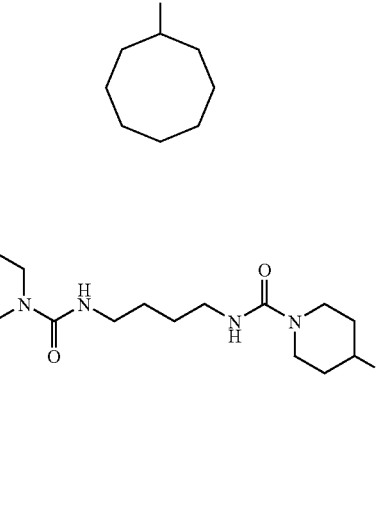 | 827 |
| 23 | 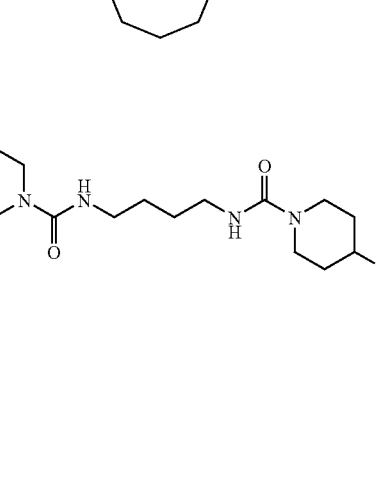 | 765 |

TABLE 1-continued

| Ex. | Structure | M/z [M + H]+ or [M + 2H]2+ |
|---|---|---|
| 24 | 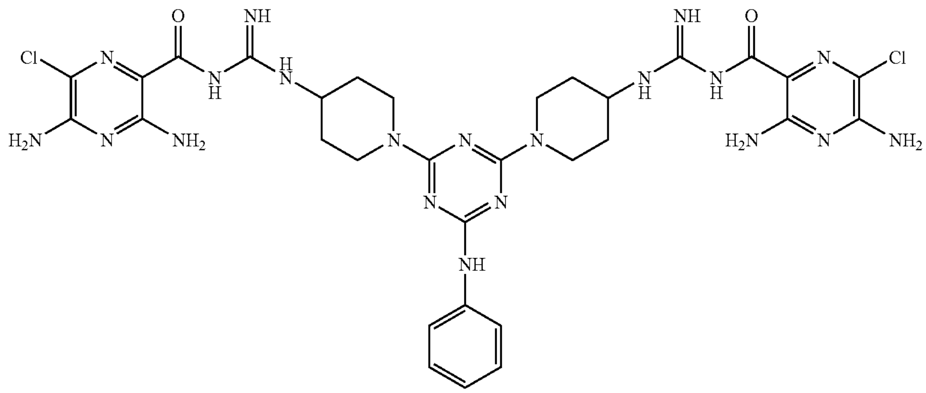 | |
| 25 | 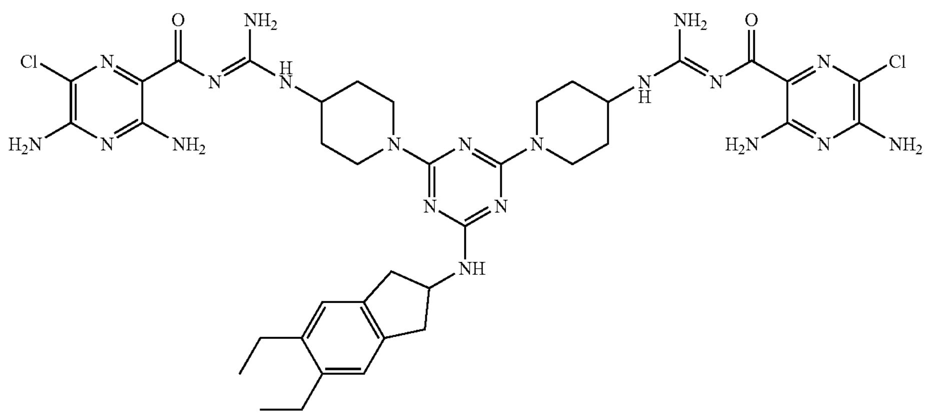 | 890 |
| 26 | 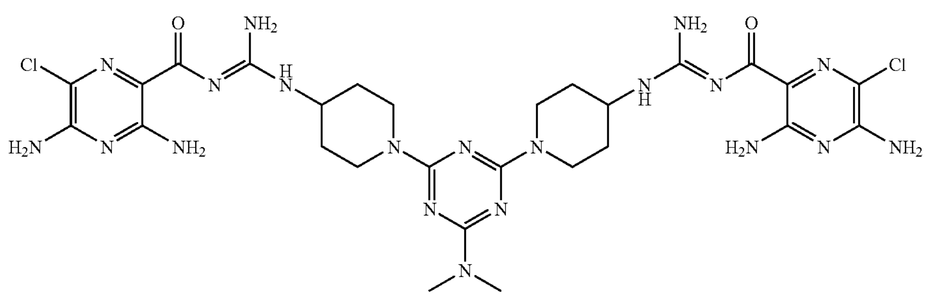 | 745 |
| 27 | 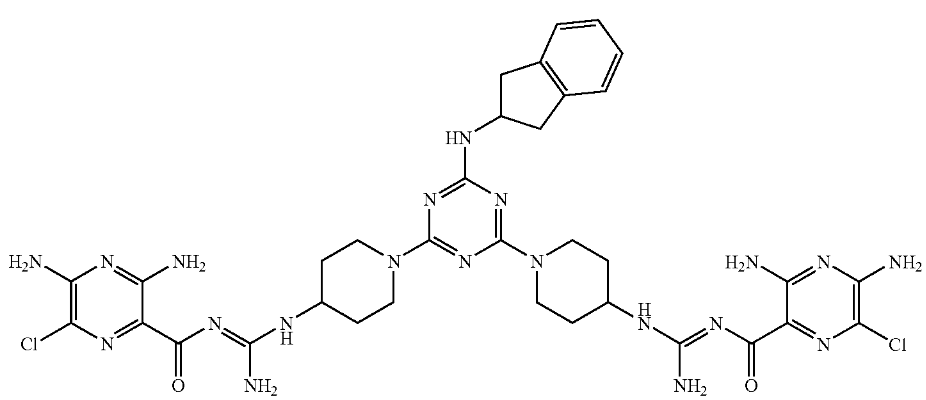 | 833 |

TABLE 1-continued

| Ex. | Structure | M/z [M + H]+ or [M + 2H]2+ |
|---|---|---|
| 28 | 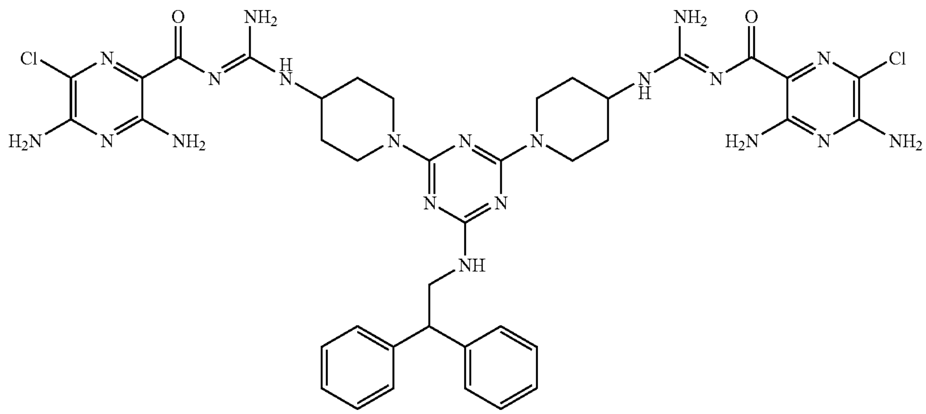 | 898 |
| 29 | 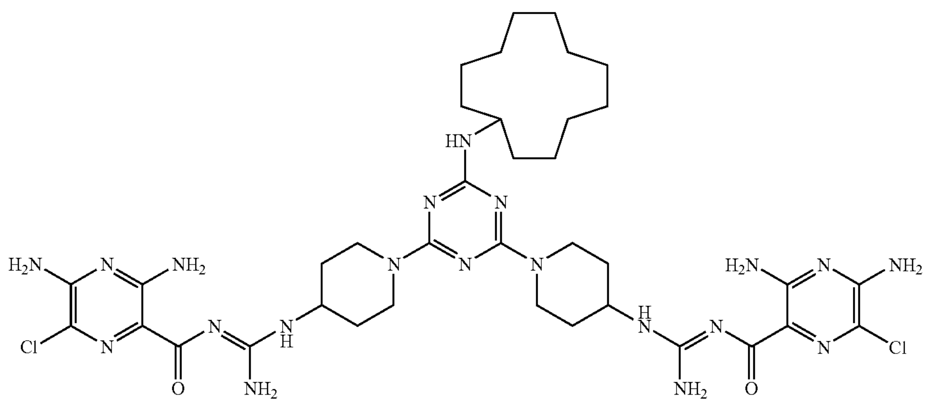 | 442 [M + 2H]2+ |
| 30 | 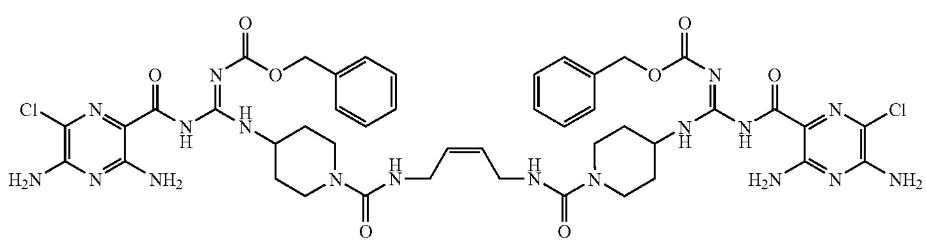 | 1031 |

General Conditions

Mass spectra are run on an open access Waters 600/ZQ HPLC/Mass Spectrometer system using electrospray ionization. [M+H]+ and [M+2H]2+ refer to monoisotopic molecular weight.

DCM dichloromethane
DIPEA diisopropylethylamine
DMF dimethylformamide
DMSO dimethyl sulfoxide
EtOAc ethyl acetate
EtOH ethanol
HATU dimethylamino-([1,2,3]triazolo[4,5-b]pyridin-3-yloxy)-methylene]-dimethyl-ammonium; hexafluorophosphate
IPA iso-propanol
MeCN acetonitrile
MeOH methanol
NMP N-methylpyrrolidone
TEA triethylamine
TFA trifluoroacetic acid
THF tetrahydrofuran Where salt forms of compounds are specified, the stoichiometry of the counterion is omitted. The skilled person will appreciate that the compound is not limited to the mono salt form and that it may exist as a disalt, trisalt or other compound:counterion stoichiometries.

Example 1

N,N'-(1,1'-(1,4-phenylenebis(methylene))bis (azanediyl) bis(oxomethylene)bis(piperidine-4,1-diyl))bis(azanediyl)bis(iminomethylene)bis(3,5-diamino-6-chloropyrazine-2-carboxamide) hydrobromide Step 1: Benzyl (1,1'-(1,4-phenylenebis(methylene)) bis(azanediyl)bis(oxomethylene) bis(piperidine-4,1-diyl))bis(azanediyl)bis((3,5-diamino-6-chloro pyrazine-2-carboxamido)methan-1-yl-1-ylidene) dicarbamate To a suspension of (4-carboxymethyl-phenyl)-acetic acid (0.5 g, 2.57 mmol) in dry DCM (10 mL) under an inert atmosphere of nitrogen is added TEA (0.7 mL, 5.14 mmol) followed by diphenylphosphoryl azide (1.1 mL, 5.14 mmol). After stirring at reflux for 2 hours, the mixture is treated with a solution of benzyl (3,5-diamino-6-chloropyrazine-2-carboxamido)(piperidin-4-ylamino)methylenecarbamate (Intermediate C) (1.72 g, 3.9 mmol) and TEA (0.7 mL, 5.14 mmol) in DCM/DMF (10 mL). The resulting mixture is heated at 38° C. overnight and then allowed to cool to room temperature. The solvent is removed in vacuo and purification of the crude product by chromatography on silica eluting with 9:1 DCM/MeOH affords the title compound.

Step 2: N,N'-(1,1'-(1,4-phenylenebis(methylene))bis (azanediyl)bis(oxomethylene)bis (piperidine-4,1-diyl))bis(azanediyl)bis(iminomethylene)bis(3,5-diamino-6-chloropyrazine-2-carboxamide) hydrobromide A suspension of benzyl (1,1'-(1,4-phenylenebis(methylene))bis(azanediyl)bis (oxomethylene)bis(piperidine-4,1-diyl))bis(azanediyl)bis((3,5-diamino-6-chloro pyrazine-2-carboxamido)methan-1-yl-1-ylidene)dicarbamate (step 1) (0.2 g, 0.18 mmol) in 33% HBr in acetic acid (5 mL) is heated at 45° C. for 5 hours. After cooling to room temperature, the solvent is removed in vacuo and the crude is treated slowly with water (approx. 20 mL) until a solid precipitates. The solid is collected by filtration and washed with water, MeOH and ether to afford the title compound. $[M+H]^+$ 813

Example 2

N,N'-(1,1'-(1,4-phenylenebis(azanediyl))bis(oxomethylene)bis(piperidine-4,1-diyl))bis(azanediyl)bis (iminomethylene)bis(3,5-diamino-6-chloropyrazine-2-carboxamide)hydrobromide This compound is prepared analogously to Example 1 by replacing 1,4-bis-isocyanatomethyl-benzene (prepared in situ) with 1,4-phenylenediisocyanate. $[M+H]^+$ 785

Example 3

N,N'-(1,1'-(cyclohexane-1,3-diylbis(methylene))bis (azanediyl)bis (oxomethylene)bis(piperidine-4,1-diyl))bis(azanediyl)bis(iminomethylene)bis(3,5-diamino-6-chloropyrazine-2-carboxamide) trifluoroacetate This compound is prepared analogously to Example 1 by replacing 1,4-bis-isocyanatomethyl-benzene (prepared in situ) with 1,3-bis-isocyanatomethyl-cyclohexane. $[M+H]^+$ 819

Example 4

N,N'-(1,1'-(1,4-phenylene)bis(oxomethylene)bis(piperidine-4,1-diyl))bis(azanediyl)bis(iminomethylene) bis(3,5-diamino-6-chloropyrazine-2-carboxamide) hydrochloride Step 1: tert-butyl(1,1'-(1,4-phenylene)bis(oxomethylene)bis(piperidine-4,1-diyl))bis(azanediyl)bis((3,5-diamino-6-chloropyrazine-2-carboxamido)methan-1-yl-1-ylidene)dicarbamate A stirred suspension of [4-(4-amino-piperidine-1-carbonyl)-phenyl]-(4-amino-piperidin-1-yl)-methanone dihydrochloride (Intermediate D) (1.1 g, 3.32 mmol) in DMF (27.5 ml) is treated with TEA (8.5 ml) and then stirred at room temperature. Intermediate A (2.5 g, 6.99 mmol) is added and the resulting mixture is heated at 60° C. for 2 days. The reaction mixture is then filtered whilst still warm under vacuum and the resulting solid is dried under vacuum to afford the product as a white solid, $[M+H]^+$ 955

Step 2

The product from step 1 is suspended in 4.0 HCl in 1,4-dioxane (2.15 ml, 8.6 mmol) and 1,4 dioxane (1 mL) at room temperature for 2 days. The solvent is removed in vacuo and the solid is freeze dried to afford the title compound. $[M+H]^+$ 755.

Example 5

N,N'-(1,1'-(6-chloro-1,3,5-triazine-2,4-diyl)bis(piperidine-4,1-diyl))bis(azanediyl)bis(iminomethylene) bis(3,5-diamino-6-chloropyrazine-2-carboxamide)

A solution of 3,5-diamino-6-chloro-N—(N-piperidin-4-ylcarbamimidoyl)pyrazine-2-carboxamide hydrochloride (Intermediate E) (8.0 g, 20.7 mmol) and dry DIPEA (25 mL) in DMF (80 mL) is cooled to 0° C. and treated with a solution of trichlorotriazine (1.9 g, 10.4 mmol) in DMF (20 mL). After stirring at 0° C. for 1 hour, the reaction mixture is allowed to warm to room temperature overnight. The mixture is then treated with MeCN (500 mL) added dropwise whilst stirring vigorously over 1 hour. The resulting fine suspension is collected by filtration under vacuum and washed with MeCN (2×250 mL). The solid is then sonicated in MeCN at 0° C., filtered and dried under vacuum to afford the title compound. $[M+H]^+$ 739

Example 6

N,N'-(1,1'-carbonylbis(piperidine-4,1-diyl)bis (azanediyl))bis(iminomethylene)bis(3,5-diamino-6-chloropyrazine-2-carboxamide)hydrochloride Step 1: tert-Butyl (1,1'-carbonylbis(piperidine-4,1-diyl)bis(azanediyl))bis((3,5-diamino-6-chloropyrazine-2-carboxamido)methan-1-yl-1-ylidene)dicarbamate hydrochloride A suspension of bis(4-aminopiperidin-1-yl)methanone (Intermediate F) (43 mg, 0.11 mmol) and Intermediate A (90 mg, 0.25 mmol) in DMF (1.5 mL) is treated with TEA (100 mg, 1.0 mmol) and heated at 70° C. for 48 hours. Purification of the reaction mixture by reverse phase column chromatography (Isolute™ C18, 0-100% acetonitrile in water—0.1%

HCl) affords the title compound in solution is 30 ml eluent (acetonitrile in water—0.1% HCl). [M+H]+ 850

Step 2: N,N'-(1,1'-carbonylbis(piperidine-4,1-diyl) bis(azanediyl))bis(iminomethylene)bis(3,5-diamino-6-chloropyrazine-2-carboxamide)hydrochloride tert-Butyl (1,1'-carbonylbis(piperidine-4,1-diyl)bis (azanediyl))bis((3,5-diamino-6-chloropyrazine-2-carboxamido)methan-1-yl-1-ylidene)dicarbamate hydrochloride (0.25 mmol) in 30 mL eluent (acetonitrile in water—0.1% HCl) is treated with TFA (4 mL) and the mixture is stirred at room temperature for 3 days. The solvent is removed in vacuo and purification by reverse phase column chromatography (Isolute™ C18, 0-100% acetonitrile in water—0.1% HCl) affords the title compound. [M+H]+ 651

Example 7

N,N'-(1,1'-(1,3,5-triazine-2,4-diyl)bis(piperidine-4,1-diyl))bis(azanediyl)bis(iminomethylene)bis(3,5-diamino-6-chloropyrazine-2-carboxamide)hydrochloride This compound is prepared analogously to Example 6 by replacing bis(4-aminopiperidin-1-yl)methanone. 4HCl (Intermediate F) with 1,1-(1,3,5-triazine-2,4-diyl)dipiperidin-4-amine. 4HCl. [M+H]+ 701

Example 8

N,N'-(1,1'-(6-(4-phenylpiperazin-1-yl)-1,3,5-triazine-2,4-diyl)bis(piperidine-4,1-diyl))bis(azanediyl)bis (iminomethylene)bis(3,5-diamino-6-chloropyrazine-2-carboxamide)acetate A solution of N,N'-(1,1'-(6-chloro-1,3,5-triazine-2,4-diyl) bis(piperidine-4,1-diyl))bis(azanediyl)bis(iminomethylene) bis(3,5-diamino-6-chloropyrazine-2-carboxamide) (Example 5) (0.25 g, 0.34 mmol) in DMF (2 mL) is treated with N-phenylpiperazine (0.275 g, 1.70 mmol) and stirred at 30° C. overnight. MeCN (3 mL) is added dropwise to the stirred mixture and the resulting yellow precipitate is collected by filtration. The precipitate is dissolved in MeOH and dry loaded onto silica. Purification by flash chromatography on silica eluting with 1:MeOH/DCM −4% NH$_3$ yields a solid which is further purified by recrystallisation from acetic acid/EtOH to afford the title compound. [M+2H]$^{2+}$ 432

Example 9

N,N'-(1,1'-(6-morpholino-1,3,5-triazine-2,4-diyl)bis (piperidine-4,1-diyl))bis(azanediyl)bis(iminomethylene)bis(3,5-diamino-6-chloropyrazine-2-carboxamide)

This compound is prepared analogously to Example 8 by replacing N-phenylpiperazine with morpholine. [M+H]+ 787

Example 10

N,N'-(1,1'-(6-(3-morpholinopropylamino)-1,3,5-triazine-2,4-diyl)bis(piperidine-4,1-diyl))bis (azanediyl)bis(iminomethylene)bis(3,5-diamino-6-chloropyrazine-2-carboxamide)trifluoroacetate A solution of N,N'-(1,1'-(6-chloro-1,3,5-triazine-2,4-diyl) bis(piperidine-4,1-diyl))bis(azanediyl)bis(iminomethylene) bis(3,5-diamino-6-chloropyrazine-2-carboxamide) (Example 5) (0.15 mg, 20 μmol) in NMP (0.5 mL) is treated with 3-(N-morpholino)propylamine (29 mg, 0.2 mmol) and then stirred at 50° C. overnight. Purification by mass directed semi-preparative HPLC affords the title compound. [M+H]+ 846

Examples 11 to 22

These compounds namely,

N,N'-(1,1'-(6-(2-(bis(2-hydroxyethyl)amino)ethylamino)-1,3,5-triazine-2,4-diyl)bis(piperidine-4,1-diyl))bis (azanediyl)bis(iminomethylene)bis(3,5-diamino-6-chloropyrazine-2-carboxamide)trifluoroacetate (Example 11);

N,N'-(1,1'-(6-(4-(azepane-1-carbonyl)piperidin-1-yl)-1,3,5-triazine-2,4-diyl)bis(piperidine-4,1-diyl))bis(azanediyl) bis(iminomethylene)bis(3,5-diamino-6-chloropyrazine-2-carboxamide)trifluoroacetate (Example 12);

N,N'-(1,1'-(6-(3-(dibutylamino)propylamino)-1,3,5-triazine-2,4-diyl)bis(piperidine-4,1-diyl))bis(azanediyl)bis (iminomethylene)bis(3,5-diamino-6-chloropyrazine-2-carboxamide) trifluoroacetate (Example 13);

N,N'-(1,1'-(6-(2-(pyridin-4-yl)ethylamino)-1,3,5-triazine-2,4-diyl)bis(piperidine-4,1-diyl))bis(azanediyl)bis(iminomethylene)bis(3,5-diamino-6-chloropyrazine-2-carboxamide) trifluoroacetate (Example 14);

N,N'-(1,1'-(6-(hexylamino)-1,3,5-triazine-2,4-diyl)bis(piperidine-4,1-diyl))bis(azanediyl)bis(iminomethylene)bis (3,5-diamino-6-chloropyrazine-2-carboxamide) trifluoroacetate (Example 15);

1-(4,6-bis(4-(3-(3,5-diamino-6-chloropyrazine-2-carbonyl) guanidino)piperidin-1-yl)-1,3,5-triazin-2-yl)piperidine-4-carboxylic acid trifluoroacetate (Example 16);

N,N'-(1,1'-(6-(4-methylpiperazin-1-yl)-1,3,5-triazine-2,4-diyl)bis(piperidine-4,1-diyl))bis(azanediyl)bis(iminomethylene)bis(3,5-diamino-6-chloropyrazine-2-carboxamide) trifluoroacetate (Example 17);

N,N'-(1,1'-(6-(dipropylamino)-1,3,5-triazine-2,4-diyl)bis (piperidine-4,1-diyl))bis(azanediyl)bis(iminomethylene) bis(3,5-diamino-6-chloropyrazine-2-carboxamide) trifluoroacetate (Example 18);

N,N'-(1,1'-(6-(cyclohexylamino)-1,3,5-triazine-2,4-diyl)bis (piperidine-4,1-diyl))bis(azanediyl)bis(iminomethylene) bis(3,5-diamino-6-chloropyrazine-2-carboxamide) trifluoroacetate (Example 19);

N,N'-(1,1'-(6-(azepan-1-yl)-1,3,5-triazine-2,4-diyl)bis(piperidine-4,1-diyl))bis(azanediyl)bis(iminomethylene)bis (3,5-diamino-6-chloropyrazine-2-carboxamide) trifluoroacetate (Example 20);

N,N'-(1,1'-(6-(cyclohexylamino)-1,3,5-triazine-2,4-diyl)bis (piperidine-4,1-diyl)) bis(azanediyl)bis(iminomethylene) bis(3,5-diamino-6-chloropyrazine-2-carboxamide)) trifluoroacetate (Example 21); and N,N'-(1,1'-(6-(cyclooctylamino)-1,3,5-triazine-2,4-diyl)bis (piperidine-4,1-diyl)) bis(azanediyl)bis(iminomethylene) bis(3,5-diamino-6-chloropyrazine-2-carboxamide) (Example 22), are prepared analogously to Example 10 by replacing 3-(N-morpholino)propylamine with the appropriate amine.

Example 23

N,N'-(1,1'-(Butane-1,4-diylbis(azanediyl))bis(oxomethylene)bis(piperidine-4,1-diyl))bis(azanediyl)bis(aminomethan-1-yl-1-ylidene)bis(3,5-diamino-6-chloropyrazine-2-carboxamide) hydrobromide

Step 1: N,N'-(1,1'-(Butane-1,4-diylbis(azanediyl))bis(oxomethylene)bis(piperidine-4,1-diyl))bis(azanediyl)bis((benzyloxycarbonylamino)methan-1-yl-1-ylidene)bis(3,5-diamino-6-chloropyrazine-2-carboxamide)

A mixture comprising benzyl (3,5-diamino-6-chloropyrazine-2-carboxamido) (methylthio)methylenecarbamate (Intermediate B) (18.6 g, 45.0 mmol) and N,N'-(butane-1,4-diyl) bis(4-aminopiperidine-1-carboxamide) (Intermediate F) (6.3 g, 15.4 mmol) in DMF (420 mL) under an inert atmosphere of nitrogen is stirred at 50° C. over 3 days. The reaction mixture is hot filtered, aminomethyl polystyrene (scavenger resin) is added and the mixture stirred at 50° C. overnight. The resin is filtered and washed with DMF, the filtrate is then concentrated in vacuo to give a solid residue which is re-dissolved up in the minimum quantity of DMF, and is added dropwise to a stirred MeCN solution at room temperature, producing a solid. This is filtered, washing with MeCN to afford the title compound as a solid. [M+H]$^+$ 1033

Step 2: N,N'-(1,1'-(Butane-1,4-diylbis(azanediyl))bis(oxomethylene)bis(piperidine-4,1-diyl))bis(azanediyl)bis(aminomethan-1-yl-1-ylidene)bis(3,5-diamino-6-chloro pyrazine-2-carboxamide) hyrobromide N,N'-(1,1'-(Butane-1,4-diylbis(azanediyl))bis(oxomethylene)bis(piperidine-4,1-diyl))bis(azanediyl)bis((benzyloxycarbonylamino)methan-1-yl-1-ylidene)bis(3,5-diamino-6-chloropyrazine-2-carboxamide) (646 mg) and 33% HBr in acetic acid (6 mL) in water (1.5 mL) is stirred at 50° C. overnight. The solvent is removed in vacuo and the resulting crude residue is purified by recrystallisation from MeOH/IPA. The residue is further purified by triturating with MeOH/EtOH followed by MeOH/IPA to afford the title compound. [M+H]$^+$ 765

Example 24

N,N'-(1,1'-(6-(phenylamino)-1,3,5-triazine-2,4-diyl)bis(piperidine-4,1-diyl)) bis(azanediyl)bis(iminomethylene)bis(3,5-diamino-6-chloropyrazine-2-carboxamide)trifluoroacetate

A solution of 3,5-diamino-6-chloro-N—(N-piperidin-4-ylcarbamimidoyl)pyrazine-2-carboxamide hydrochloride (Intermediate E) (200 mg, 0.52 mmol), (4,6-dichloro-[1,3,5]triazin-2-yl)-phenyl-amine (60 mg, 0.25 mmol) and DIPEA (205 mg, 1.6 mmol) in NMP (4 mL) is stirred at 35° C. overnight. The reaction mixture is then added dropwise to MeCN and the resulting white solid is collected by filtration. The solid is dissolved in 1:1 MeCN:water (0.1% TFA) (60 mL), cooled and allowed to stand for 4 days. The resulting suspension is filtered to afford the title compound as a solid.

Example 25

N,N'-(1,1'-(6-(5,6-diethyl-2,3-dihydro-1H-inden-2-ylamino)-1,3,5-triazine-2,4-diyl)bis(piperidine-4,1-diyl))bis(azanediyl)bis(aminomethan-1-yl-1-ylidene)bis(3,5-diamino-6-chloropyrazine-2-carboxamide)

N,N'-(1,1'-(6-chloro-1,3,5-triazine-2,4-diyl))bis(piperidine-4,1-diyl))bis(azanediyl)bis(iminomethylene)bis(3,5-diamino-6-chloropyrazine-2-carboxamide) (Example 5) (250 mg, 0.34 mmol) and 5,6-diethylindan-2-ylamine hydrochloride (225 mg, 1.00 mmol; see Prashad et al., *Org Process Res Dev*, Vol. 10, No. 1, pp. 135-141 (2006)) are suspended in DMF (1 ml) with DIPEA (350 µl, 260 mg, 2.00 mmol) in a 0.5-2.0 ml Biotage microwave vial. The vial is sealed and, the reaction heated using microwave irradiation for 24 hours 60° C., followed by 22.5 hours at 70° C. Precipitation by addition of the reaction mixture to acetonitrile (50 ml) affords a mixture of the title compound and N,N'-(1,1'-(6-(dimethylamino)-1,3,5-triazine-2,4-diyl)bis(piperidine-4,1-diyl))bis(azanediyl)bis(aminomethan-1-yl-1-ylidene)bis(3,5-diamino-6-chloropyrazine-2-carboxamide) as a grey solid. Purification by mass-directed preparative HPLC followed by trituration with diethyl ether affords the title compound as a pale yellow powder. [M+H]$^+$ 890

Example 26

N,N'-(1,1'-(6-(Dimethylamino)-1,3,5-triazine-2,4-diyl)bis(piperidine-4,1-diyl))bis(azanediyl)bis(aminomethan-1-yl-1-ylidene)bis(3,5-diamino-6-chloropyrazine-2-carboxamide)

This compound is prepared as a by-product in the synthesis of Example 25.
[M+H]$^+$ 745

Examples 27-29

These compounds namely,
N,N'-(1,1'-(6-(2,3-dihydro-1H-inden-2-ylamino)-1,3,5-triazine-2,4-diyl)bis(piperidine-4,1-diyl))bis(azanediyl)bis(aminomethan-1-yl-1-ylidene)bis(3,5-diamino-6-chloropyrazine-2-carboxamide) (Example 27);
N,N'-(1,1'-(6-(2,2-diphenylethylamino)-1,3,5-triazine-2,4-diyl)bis(piperidine-4,1-diyl))bis(azanediyl)bis(aminomethan-1-yl-1-ylidene)bis(3,5-diamino-6-chloropyrazine-2-carboxamide) (Example 28); and
N,N'-(1,1'-(6-(cyclododecylamino)-1,3,5-triazine-2,4-diyl)bis(piperidine-4,1-diyl))bis(azanediyl)bis(aminomethan-1-yl-1-ylidene)bis(3,5-diamino-6-chloropyrazine-2-carboxamide) (Example 29),
are prepared from N,N'-(1,1'-(6-chloro-1,3,5-triazine-2,4-diyl)bis(piperidine-4,1-diyl))bis(azanediyl)bis(iminomethylene)bis(3,5-diamino-6-chloropyrazine-2-carboxamide) (Example 5) analogously to Example 25 by replacing 5,6-diethylindan-2-ylamine hydrochloride with the appropriate amine.

Example 30

Benzyl (1,1'-(Z)-but-2-ene-1,4-diylbis(azanediyl)bis(oxomethylene)bis (piperidine-4,1-diyl))bis(azanediyl)bis((3,5-diamino-6-chloropyrazine-2-carboxamido)methan-1-yl-1-ylidene)dicarbamate

A solution of ((Z)-4-phenoxycarbonylamino-but-2-enyl)-carbamic acid phenyl ester (Intermediate J) (325 mg, 1.0 mmol), benzyl (3,5-diamino-6-chloropyrazine-2-carboxamido)(piperidin-4-ylamino)methylenecarbamate (Intermediate C) (1.25 g, 2.2 mmol) and TEA (0.6 ml, 4.4 mmol) in DMF (4 ml) is heated at 60° C. overnight. The mixture is treated with water and allowed to stand at room temperature for 10 minutes. IPA (20 ml) is added to the resulting solid and the mixture is filtered to afford the title compound as a solid. [M+H]$^+$ 1031

Preparation of Intermediates

Intermediate A tert-Butyl (3,5-diamino-6-chloropyrazine-2-carboxamido)(methylthio)methylene carbamate

Step 1: Lithium 3,5-diamino-6-chloro-pyrazine-2-carboxylic acid

A stirred suspension of 3,5-diamino-6-chloro-pyrazine-2-carboxylic acid methyl ester (110 g, 542.9 mmol) in MeOH (500 mL) at 5-10° C. (ice-bath) is treated dropwise with a suspension of lithium hydroxide (46.6 g, 1111 mmol) in water (500 mL). The reaction mixture is heated to 50° C. for 5 hours then cooled to room temperature and stirred overnight. The resulting precipitate is collected by filtration and dried in a vacuum oven to afford the title compound as the lithium salt (di-hydrate). [M−Li]⁻ 187

Step 2: tert-Butyl amino(methylthio)methylenecarbamate

A stirred suspension of S-methyl-iso-thiourea sulphate (10 g, 35.9 mmol) in toluene (75 mL) is treated with 4 M NaOH (15 mL) at room temperature. To the two-phase mixture is added di-tert.butyl dicarbonate (3.27 g, 15 mmol) in one portion. The reaction mixture is stirred at room temperature for 1 hour, then heated to 60° C. overnight. The organic portion is separated, washed with brine solution, then dried over $Na_2SO_4$, filtered and concentrated in vacuo to a viscous oil, which crystallised under high vacuum to afford the title compound as a colourless solid.

Step 3: tert-Butyl (3,5-diamino-6-chloropyrazine-2-carboxamido)(methylthio)methylene carbamate A stirring suspension of lithium 3,5-diamino-6-chloro-pyrazine-2-carboxylic acid (22.6 g, 98.03 mmol) in DMF (400 mL) is treated portionwise with HATU (41 g, 107.83 mmol), under an inert atmosphere of nitrogen. The reaction mixture is stirred at room temperature for 2 hours and then tert-butyl amino(methylthio)methylenecarbamate (20.5 g, 107.83 mmol) is added portion wise over a period of 10 minutes. The reaction mixture is stirred at room temperature for a further 1.5 hours then heated to 50° C. and stirred overnight. The resulting precipitate is hot filtered, washing with water and dried in a vacuum oven (40° C.) overnight to afford the title compound. [M+H]⁺ 361

Intermediate B Benzyl (3,5-diamino-6-chloropyrazine-2-carboxamido)(methylthio)methylenecarbamate To a stirred solution of 1-(3,5-diamino-6-chloro-pyrazine-2-carbonyl)-2-methyl-isothiourea hydroiodide (Intermediate I) (50 g, 0.129 mol) in dry THF (1 L) is added TEA (18 mL, 0.129 mol), followed by N-(benzyloxycarbonyloxy)-succinimide (32.1 g, 0.129 mol). The reaction mixture is then heated to reflux (66° C.) for 6 hours. The reaction is allowed to cool to room temperature, then concentrated in vacuo to a yellow solid. The crude is suspended in EtOAc (500 mL) and water (500 mL) and is triturated vigorously for a period of 30 minutes. The resulting suspension is filtered and dried in a vacuum oven (40° C.) over $P_2O_5$ to give the product as a pale yellow solid. [M+H]⁺ 395

Intermediate C Benzyl (3,5-diamino-6-chloropyrazine-2-carboxamido)(piperidin-4-ylamino)methylenecarbamate

Step 1: tert-Butyl 4-(2-(benzyloxycarbonyl)-3-(3,5-diamino-6-chloropyrazine-2-carbonyl)guanidino)piperidine-1-carboxylate A suspension of benzyl (3,5-diamino-6-chloropyrazine-2-carboxamido)(methylthio)methylenecarbamate (Intermediate B) (6.7 g, 17 mmol) and 4-amino-1-Boc-piperidine (4.1 g, 20.4 mmol) in dry THF (150 mL) is heated at reflux overnight. The solvent is removed in vacuo and a solid forms on concentration. The solid is separated and retained and the remaining mother liquor is concentrated to form a solid. The solid is partitioned between EtOAc and water and the organic portion is dried (MgSO₄) and part concentrated in vacuo and then left to crystallise. The crystals are filtered and combined with the retained solid to afford the title product. [M+H]⁺ 547

Step 2: Benzyl (3,5-diamino-6-chloropyrazine-2-carboxamido)(piperidin-4-ylamino)methylenecarbamate A suspension of tert-butyl 4-(2-(benzyloxycarbonyl)-3-(3,5-diamino-6-chloropyrazine-2-carbonyl)guanidino)piperidine-1-carboxylate (Step 1) (6.3 g, 11.5 mmol) in dioxane (250 mL) and MeOH (small volume) is treated with 4 M HCl in dioxane (40 mL) and left to stir overnight at 40° C. The resulting suspension is filtered and the solid is partitioned between water (800 mL) and EtOAc (800 mL). 1 M NaOH is added to adjust the pH to pH 8 and the organic portion is separated, dried (MgSO₄) and concentrated in vacuo to afford the title compound. [M+H]⁺ 447

Intermediate D [4-(4-Amino-piperidine-1-carbonyl)-phenyl]-(4-amino-piperidin-1-yl)-methanone Step 1

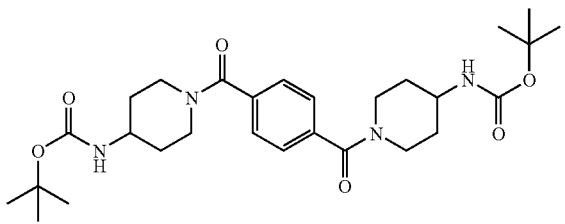

Under an inert atmosphere of nitrogen a solution of terephthaloyl chloride (50.7 g, 0.249 mol) in DMF (200 mL) is added slowly to a mixture of 4-(N-Boc-amino)piperidine (100 g, 0.499 mol) and triethylamine (104 mL, 0.749 mol) in DMF (800 mL). The reaction mixture is allowed to stir at room temperature overnight. A white suspension forms and the resulting mixture is quenched slowly with saturated NaHCO₃ solution (500 mL) and water (500 mL). The resulting suspension is stirred for 30 minutes and is filtered under vacuum to afford a white solid. The solid is dried under vacuum at 45° C. to yield the required product. [M+H]⁺ 531

Step 2: [4-(4-Amino-piperidine-1-carbonyl)-phenyl]-(4-amino-piperidin-1-yl)-methanone dihydrochloride A mixture comprising the product from Step 1 (50 g, 0.09 mol) in 1,4-dioxane (236 ml, is treated with 4 M HCl in dioxane (236 ml). The resulting suspension is allowed to stir at room temperature overnight. The resulting suspension is filtered under vacuum and washed with diethyl ether (3×200 ml) to yield the desired product. The recovered solid is dried under vacuum for 2 days to afford the title compound. [M+H]+ 331

Alternatively, Step 2 can be carried out in the presence of TMSI in DCM at room temperature to afford [4-(4-amino-piperidine-1-carbonyl)-phenyl]-(4-amino-piperidin-1-yl)-methanone Intermediate D Alternative Synthetic Route

[4-(4-Amino-piperidine-1-carbonyl)-phenyl]-(4-amino-piperidin-1-yl)-methanone

Step 1

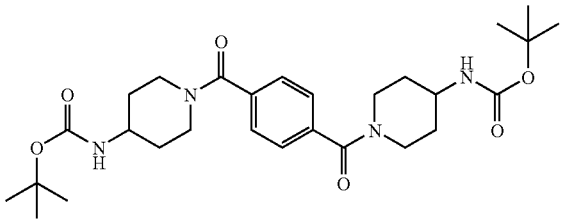

A solution of terephthaloyl chloride (1.02 g, 5.0 mmol) in DMF (10 mL) under an inert atmosphere of argon is treated dropwise with a solution of 4-(N-Boc-amino)piperidine (2.00 g, 10.0 mmol) over 20 minutes. The reaction mixture is allowed to stir at room temperature for 40 minutes and then TEA (2.09 mL, 15.0 mmol) is added dropwise. A white suspension forms and stirring continues for 2 hours. The resulting mixture is washed with saturated NaHCO3 solution (50 mL) and water (100 mL). The resulting mixture is filtered under vacuum using phase separating paper to afford a white solid. The solid is dried under vacuum at 45° C. to yield the required product. [M+H]+ 531

Step 2: [4-(4-Amino-piperidine-1-carbonyl)-phenyl]-(4-amino-piperidin-1-yl)-methanone dihydrobromide A mixture comprising the product from Step 1 (1.34 g, 2.53 mmol) in 33% HBr in acetic acid (13.4 mL, 25.3 mmol) is stirred at room temperature overnight. The resulting suspension is diluted with DCM (10-20 mL) and filtered under vacuum. The recovered solid is dried under vacuum for 2 days to afford the title compound. [MH+ 331.16]

Alternatively, Step 2 can be carried out in the presence of 4 M HCl in dioxane to afford [4-(4-amino-piperidine-1-carbonyl)-phenyl]-(4-amino-piperidin-1-yl)-methanone dihydrochloride.

Intermediate E 3,5-Diamino-6-chloro-N—(N-piperidin-4-ylcarbamimidoyl)pyrazine-2-carboxamide hydrochloride A solution of 1-(3,5-diamino-6-chloro-pyrazine-2-carbonyl)-2-methyl-isothiourea hydroiodide (7.2 g, 18.4 mmol) and 4-amino-1-Boc-piperidine (5.5 g, 27.5 mmol) in DMF (40 mL) is stirred and heated at 50° C. for 4 hours. The mixture is diluted with water (150 mL) and sonicated for 2 hours. The resulting suspension is collected by filtration and suspended in 4 M HCl in dioxane (40 mL). MeOH (20 mL) is added and the mixture is stirred at room temperature overnight and then filtered. The solid is washed with EtOH (2×10 mL) and dried to afford the title compound. [M+H]+ 313

Intermediate F
Bis(4-aminopiperidin-1-yl)methanone hydrochloride

Step 1: tert-Butyl 1,1'-carbonylbis(piperidine-4,1-diyl)dicarbamate

A cooled (0° C.), stirred solution of 4-N-Boc-amino-piperidine (2.0 g, 10.2 mmol) in DCM (8 mL) is treated dropwise with a solution of triphosgene (0.503 g, 1.7 mmol) in DCM (8 mL). The mixture is allowed to warm to room temperature and then stirring continued for a further 2 hours after which time the mixture is partitioned between DCM and 1 M NaOH. The organic portion is separated, washed with 1 M HCl, water, saturated NaHCO3 dried and concentrated in vacuo to afford the title compound. MH+ 427

Step 2: Bis(4-aminopiperidin-1-yl)methanone

A solution of tert-butyl 1,1'-carbonylbis(piperidine-4,1-diyl)dicarbamate (1.0 g, 2.3 mmol) in 4 M HCl in dioxane (3 mL) and MeOH (5 mL) is stirred at room temperature overnight. The solvent is removed in vacuo to afford the title compound as a white solid. [M+H]+ 227

Intermediate G 1,1'-(1,3,5-triazine-2,4-diyl)dipiperidin-4-amine hydrochloride

This compound is prepared analogously to Intermediate F by replacing triphosgene with 2,4-dichloro-1,3,5-triazine. Step 1 is carried out in THF.

Intermediate H N,N'-(Butane-1,4-diyl)bis(4-aminopiperidine-1-carboxamide)

Step 1: tert-Butyl 1,1'-(butane-1,4-diylbis(azanediyl))bis(oxomethylene)bis(piperidine-4,1-diyl)dicarbamate A solution of 4-N-Boc-aminopiperidine (1.0 g, 4.99 mmol) and dry DCM (20 mL) is treated with 1,4-diisocyanatobutane (317 µL, 2.49 mmol) and allowed to stir at room temperature overnight. The resulting suspension is filtered and washed with DCM to afford the title compound. [M+H]+ 541

Step 2: N,N'-(Butane-1,4-diyl)bis(4-aminopiperidine-1-carboxamide)

A suspension of tert-butyl 1,1'-(butane-1,4-diylbis(azanediyl))bis(oxomethylene) bis(piperidine-4,1-diyl)dicarbamate (1.26 g, 2.33 mmol) in MeOH (10 mL) is treated with TFA (25 mL) followed by water (catalytic amount) and the resulting solution is stirred at room temperature for 5 days. DCM, MeOH and TFA are removed in vacuo and the residue is diluted with a small volume of water and neutralised by addition of 4 M NaOH. The mixture is left to crystallise in a cool environment (fridge) overnight to resulting crystals are filtered and dried in vacuo to afford the title compound. [M+H]+ 341

Intermediate I 1-(3,5-Diamino-6-chloro-pyrazine-2-carbonyl)-2-methyl-isothiourea A stirring suspension of tert-butyl (3,5-diamino-6-chloropyrazine-2-carboxamido) (methylthio)methylene carbamate (Intermediate A) (200 mg, 0.554 mmol) in DCM (10 mL) is treated dropwise with TFA (0.412 mL, 5.543 mmol) dissolved in DCM (5 mL), resulting in a yellow solution. The reaction mixture is stirred at room temperature for 4 hours, the solvents are removed in vacuo to give a yellow oil which contains a small amount of solid. The oil is dissolved in water and the undissolved solid is removed by filtration. The aqueous filtrate is basified to pH 9 with NaHCO$_3$ and the resulting precipitate is collected by filtration and dried in a vacuum oven (40° C.) overnight to afford the title compound. [M+H]$^+$ 261

Intermediate J
((Z)-4-Phenoxycarbonylamino-but-2-enyl)-carbamic acid phenyl ester A stirred solution of phenyl chloroformate (3.4 g, 22 mmol) in DCM (70 ml) is treated dropwise with a solution of pyridine (1.9 g, 24 mmol) in DCM (10 ml). To this mixture is added (Z)-but-2-ene-1,4-diamine (prepared according to the procedure of Fabiano et al, Synthesis, (2), 190(2); 1987) in DCM (20 ml) dropwise over 15 minutes. The resulting mixture is stirred at room temperature for 4 hours and partitioned between DCM and water. The organic portion is separated and washed with water, 0.5M HCl (2×), NaHCO$_3$(aq) (2×), dried (MgSO$_4$) and concentrated in vacuo. Purification of the crude product by chromatography on silica eluting with 0-1% MeOH in DCM affords the title compound; [M+H]$^+$ 327.

We claim:

1. A compound, wherein the compound is of formula (Ia):

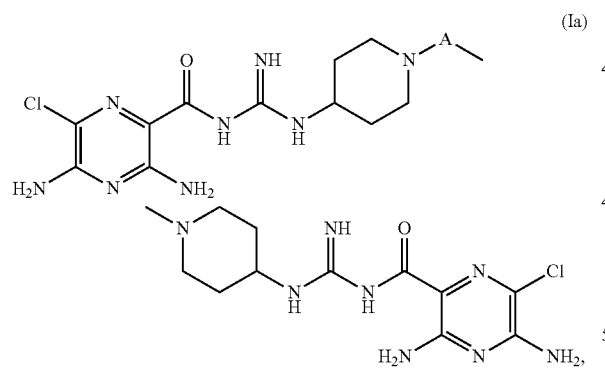

(Ia)

or pharmaceutically acceptable salt thereof,
wherein A is selected from:

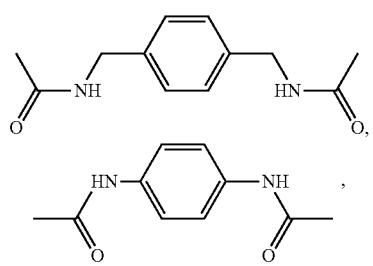

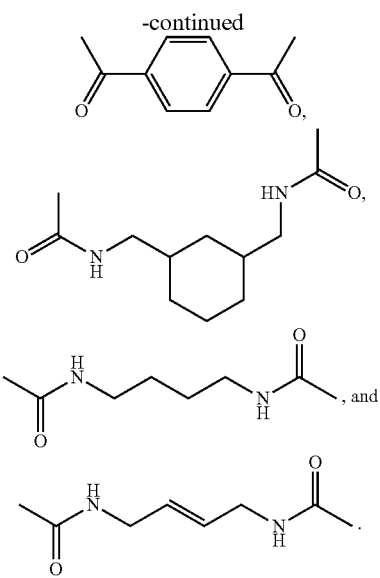

2. The compound or its pharmaceutically acceptable salt according to claim 1, selected from
N,N'-(1,1'-(1,4-phenylenebis(methylene))bis(azanediyl) bis(oxomethylene)bis(piperidine-4,1-diyl))bis (azanediyl)bis(iminomethylene)bis(3,5-diamino-6-chloropyrazine-2-carboxamide);
N,N'-(1,1'-(1,4-phenylenebis(azanediyl))bis(oxomethylene)bis(piperidine-4,1-diyl))bis(azanediyl)bis(iminomethylene)bis(3,5-diamino-6-chloropyrazine-2-carboxamide);
N,N'-(1,1'-(cyclohexane-1,3-diylbis(methylene))bis (azanediyl)bis (oxomethylene)bis(piperidine-4,1-diyl)) bis(azanediyl)bis(iminomethylene)bis(3,5-diamino-6-chloropyrazine-2-carboxamide);
N,N'-(1,1'-(1,4-phenylene)bis(oxomethylene)bis(piperidine-4,1-diyl))bis(azanediyl)bis(iminomethylene)bis (3,5-diamino-6-chloropyrazine-2-carboxamide);
N,N'-(1,1'-carbonylbis(piperidine-4,1-diyl)bis (azanediyl))bis(iminomethylene)bis(3,5-diamino-6-chloropyrazine-2-carboxamide);
N,N'-(1,1'-(Butane-1,4-diyl)bis(azanediyl))bis(oxomethylene)bis(piperidine-4,1-diyl))bis(azanediyl)bis(aminomethan-1-yl-1-ylidene)bis(3,5-diamino-6-chloropyrazine-2-carboxamide); and
Benzyl (1,1'-(Z)-but-2-ene-1,4-diylbis(azanediyl)bis(oxomethylene)bis(piperidine-4,1-diyl))bis(azanediyl)bis ((3,5-diamino-6-chloropyrazine-2-carboxamido) methan-1-yl-1-ylidene)dicarbamate.

3. A pharmaceutical composition, comprising:
the compound according to claim 1, or its pharmaceutically acceptable salt and
a pharmaceutically acceptable excipient.

4. A method of treating a subject with asthma, comprising:
administering to a patient in need thereof of an effective amount of the compound according to claim 1.

5. A pharmaceutical combination, comprising:
the compound according to claim 1 and an anti-inflammatory, bronchodilatory, antihistamine or anti-tussive drug substance.

6. The compound or its pharmaceutically acceptable salt according to claim 1, represented by N,N'-(1,1'-(1,4-phenylenebis(methylene))bis(azanediyl) bis(oxomethylene)bis(piperidine-4,1-diyl))bis(azanediyl)bis(iminomethylene)bis(3,5-diamino-6-chloropyrazine-2-carboxamide).

7. The compound or its pharmaceutically acceptable salt according to claim 1, represented by N,N'-(1,1'-(1,4-phenylenebis(azanediyl))bis(oxomethylene)bis(piperidine-4,1-diyl))bis(azanediyl)bis(iminomethylene)bis(3,5-diamino-6-chloropyrazine-2-carboxamide).

8. The compound or its pharmaceutically acceptable salt according to claim 1, represented by N,N'-(1,1'-(cyclohexane-1,3-diylbis(methylene))bis(azanediyl)bis (oxomethylene)bis(piperidine-4,1-diyl))bis(azanediyl)bis(iminomethylene)bis(3,5-diamino-6-chloropyrazine-2-carboxamide).

9. The compound or its pharmaceutically acceptable salt according to claim 1, represented by N,N'-(1,1'-(1,4-phenylene)bis(oxomethylene)bis(piperidine-4,1-diyl))bis (azanediyl)bis(iminomethylene)bis(3,5-diamino-6-chloropyrazine-2-carboxamide).

10. The compound or its pharmaceutically acceptable salt according to claim 1, represented by N,N'-(1,1'-carbonylbis(piperidine-4,1-diyl)bis(azanediyl))bis (iminomethylene)bis (3,5-diamino-6-chloropyrazine-2-carboxamide).

11. The compound or its pharmaceutically acceptable salt according to claim 1, represented by N,N'-(1,1'-(Butane-1,4-diylbis(azanediyl))bis(oxomethylene) bis(piperidine-4,1-diyl))bis(azanediyl)bis(aminomethan-1-yl-1-ylidene)bis(3,5-diamino-6-chloropyrazine-2-carboxamide).

12. The compound or its pharmaceutically acceptable salt according to claim 1, represented by Benzyl (1,1'-(Z)-but-2-ene-1,4-diylbis(azanediyl)bis(oxomethylene)bis (piperidine-4,1-diyl))bis(azanediyl)bis((3,5-diamino-6-chloropyrazine-2-carboxamido)methan-1-yl-1-ylidene)dicarbamate.

13. A pharmaceutical composition, comprising:
the compound according to claim 6, or its pharmaceutically acceptable salt and
a pharmaceutically acceptable excipient.

14. A pharmaceutical composition, comprising:
the compound according to claim 7, or its pharmaceutically acceptable salt and
a pharmaceutically acceptable excipient.

15. A pharmaceutical composition, comprising:
the compound according to claim 8, or its pharmaceutically acceptable salt and
a pharmaceutically acceptable excipient.

16. A pharmaceutical composition, comprising:
the compound according to claim 9, or its pharmaceutically acceptable salt and
a pharmaceutically acceptable excipient.

17. A pharmaceutical composition, comprising:
the compound according to claim 10, or its pharmaceutically acceptable salt and
a pharmaceutically acceptable excipient.

18. A pharmaceutical composition, comprising:
the compound according to claim 11, or its pharmaceutically acceptable salt and
a pharmaceutically acceptable excipient.

19. A pharmaceutical composition, comprising:
the compound according to claim 12, or its pharmaceutically acceptable salt and
a pharmaceutically acceptable excipient.

* * * * *